US010574966B2

(12) United States Patent
Lodato et al.

(10) Patent No.: US 10,574,966 B2
(45) Date of Patent: Feb. 25, 2020

(54) METHOD FOR MODIFYING AT LEAST ONE FRAME VIDEO OF A DIGITAL VIDEO STREAM TO BE DISPLAYED ON A DISPLAYING AREA AND RELATED SYSTEM

(71) Applicant: Consiglio Nazionale Delle Ricerche, Rome (IT)

(72) Inventors: Carmelo Lodato, Rome (IT); Patrizia Ribino, Rome (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 16/096,978

(22) PCT Filed: Apr. 27, 2017

(86) PCT No.: PCT/IT2017/000089
§ 371 (c)(1),
(2) Date: Oct. 26, 2018

(87) PCT Pub. No.: WO2017/187468
PCT Pub. Date: Nov. 2, 2017

(65) Prior Publication Data
US 2019/0116353 A1 Apr. 18, 2019

(30) Foreign Application Priority Data
Apr. 27, 2016 (IT) .................. 10201642744

(51) Int. Cl.
*H04N 13/167* (2018.01)
*H04N 13/383* (2018.01)
*A61B 3/024* (2006.01)

(52) U.S. Cl.
CPC .......... *H04N 13/167* (2018.05); *A61B 3/024* (2013.01); *H04N 13/383* (2018.05)

(58) Field of Classification Search
CPC ..... H04N 13/167; H04N 13/383; A61B 3/024
See application file for complete search history.

(56) References Cited

U.S. PATENT DOCUMENTS

| 2010/0045933 A1* | 2/2010 | Eberl | A61B 3/113 351/210 |
| 2011/0194075 A1* | 8/2011 | Weleber | A61B 3/024 351/224 |

(Continued)

OTHER PUBLICATIONS

International Search Report dated Apr. 10, 2017 for International Application No. PCT/IT2017/000089 in 2 pages.

(Continued)

*Primary Examiner* — Jonathan R Messmore
(74) *Attorney, Agent, or Firm* — Knobbe, Martens, Olson & Bear LLP

(57) ABSTRACT

The present invention relates to a method for modifying at least one video frame of a digital video stream to be displayed on a display area. Each correction scheme has one or more specific digital filters based on visual defects perceived by a person with respect to a video frame portion, is configured when predetermined conditions are met and reconfigured whenever the origin position of an eye reference system associated with a respective eye is different from the position of the same origin in said predetermined conditions and/or the orientation of said eye reference system is different from the orientation of the same eye reference system in said predetermined conditions. The generation of a multiview digital video stream, subsequent to the application of the first correction scheme and/or the second correction scheme, and the displaying of said digital video stream by a multiview stereoscopic or stereoscopic video system allow to the two eyes of a person to observe a respective succession of video frames, wherein the content of the video frames of each sequence of video frames has (Continued)

been modified on the basis of visual defects of a respective eye of said subject suffering from a degenerative disease of the retina, so that said subject has a visual perception, in binocular vision, improved or corrected.

10 Claims, 12 Drawing Sheets

(56) References Cited

U.S. PATENT DOCUMENTS

| | | |
|---|---|---|
| 2013/0057644 A1 | 3/2013 | Stefanoski et al. |
| 2015/0257967 A1 | 9/2015 | Simmons |
| 2016/0314564 A1* | 10/2016 | Jones .................... G06T 15/04 |
| 2017/0325676 A1* | 11/2017 | Lichtenauer ......... A61B 3/0008 |

OTHER PUBLICATIONS

Written Opinion of the International Searching Authority dated Apr. 10, 2017 for International Application No. PCT/IT2017/000089 in 9 pages.

\* cited by examiner

```
┌─────────────────────────────────────────────────────────────────────┐
│           ACQUIRING A FIRST DIGITAL VIDEO STREAM INCLUDING ONE       │
│                 SUCCESSION OF FIRST VIDEO FRAMES                     │
└─────────────────────────────────────────────────────────────────────┘
                                   │
┌─────────────────────────────────────────────────────────────────────┐
│  INDIVIDUATING WITH RESPECT TO SAID FIRST DIGITAL VIDEO STREAM, FOR THE RIGHT │
│     EYE, SHAPE, SIZE AND LOCATION OF AT LEAST A FIRST VIDEO FRAME PORTION    │
│  ON WHICH A FIRST VISUAL DEFECT IS PERCEIVED BY A PERSON AND/OR FOR THE LEFT │
│        EYE, SHAPE, SIZE AND LOCATION OF AT LEAST A SECOND VIDEO FRAME        │
│        PORTION IN WHICH A SECOND DEFECT VISUAL IS PERCEIVED BY A PERSON      │
└─────────────────────────────────────────────────────────────────────┘
                                   │
┌─────────────────────────────────────────────────────────────────────┐
│          DETERMINING FOR SAID AT LEAST A FIRST VIDEO FRAME PORTION            │
│       ONE OR MORE FIRST DIGITAL FILTERS AND/OR FOR SAID AT LEAST A SECOND     │
│             VIDEO FRAME PORTION ONE OR MORE SECOND DIGITAL FILTERS            │
└─────────────────────────────────────────────────────────────────────┘
                                   │
┌─────────────────────────────────────────────────────────────────────┐
│          CONFIGURING A RIGHT CORRECTION SCHEME FOR THE RIGHT EYE              │
│       INCLUDING SAID ONE OR MORE FIRST DIGITAL FILTERS AND/OR FOR THE         │
│           LEFT EYE A LEFT CORRECTION SCHEME INCLUDING SAID ONE OR             │
│                          MORE SECOND DIGITAL FILTERS                          │
└─────────────────────────────────────────────────────────────────────┘
                                   │
┌─────────────────────────────────────────────────────────────────────┐
│                 ACQUIRING A SECOND DIGITAL VIDEO STREAM                       │
│             INCLUDING A SUCCESSION OF SECOND VIDEO FRAMES                     │
└─────────────────────────────────────────────────────────────────────┘
                                   │
┌─────────────────────────────────────────────────────────────────────┐
│ CALCULATING FOR THE RIGHT EYE A FIRST ORIGIN POSITION AND A FIRST ORIENTATION │
│ OF A RIGHT EYE REFERENCE SYSTEM WITH RESPECT TO A DISPLAY REFERENCE SYSTEM    │
│ AND/OR FOR THE LEFT EYE A SECOND ORIGIN POSITION AND A SECOND ORIENTATION     │
│ OF A LEFT EYE REFERENCE SYSTEM WITH RESPECT TO A DISPLAY REFERENCE SYSTEM     │
└─────────────────────────────────────────────────────────────────────┘
                                   │
┌─────────────────────────────────────────────────────────────────────┐
│ COMPARING THE FIRST ORIGIN POSITION OF THE RIGHT EYE REFERENCE SYSTEM WITH A  │
│    PREDETERMINED FIRST ORIGIN POSITION OF THE ORIGIN ITSELF AND/OR THE FIRST  │
│   ORIENTATION OF THE RIGHT EYE REFERENCE SYSTEM WITH A PREDETERMINED FIRST    │
│    ORIENTATION OF THE RIGHT EYE REFERENCE SYSTEM ITSELF, AND/OR THE SECOND    │
│      ORIGIN POSITION OF THE LEFT EYE REFERENCE SYSTEM WITH A PREDETERMINED    │
│      SECOND POSITION OF THE ORIGIN ITSELF AND/OR THE SECOND ORIENTATION       │
│   OF THE LEFT EYE REFERENCE SYSTEM WITH A PREDETERMINED SECOND ORIENTATION    │
│                    OF THE LEFT EYE REFERENCE SYSTEM ITSELF                    │
└─────────────────────────────────────────────────────────────────────┘
```

Fig. 2A

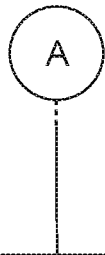

WHEN SAID FIRST POSITION OF THE ORIGIN OF SAID RIGHT EYE REFERENCE SYSTEM IS DIFFERENT FROM SAID PREDETERMINED FIRST ORIGIN POSITION AND/OR SAID FIRST ORIENTATION OF THE RIGHT EYE REFERENCE SYSTEM IS DIFFERENT FROM SAID PREDETERMINED FIRST ORIENTATION, RECONFIGURING SAID RIGHT CORRECTION SCHEME BASED ON SAID FIRST ORIGIN POSITION AND/OR SAID FIRST ORIENTATION, AND/OR WHEN SAID SECOND POSITION OF THE ORIGIN OF SAID LEFT EYE REFERENCE SYSTEM IS DIFFERENT FROM SAID PREDETERMINED SECOND ORIGIN POSITION AND/OR SAID SECOND ORIENTATION IS DIFFERENT FROM SAID PREDETERMINED SECOND ORIENTATION, RECONFIGURING SAID LEFT CORRECTION SCHEME BASED ON SAID SECOND ORIGIN POSITION AND/OR SAID SECOND ORIENTATION

APPLYING SAID RIGHT CORRECTION SCHEME TO AT LEAST A SECOND VIDEO FRAME OF SAID SECOND DIGITAL VIDEO STREAM SO AS TO OBTAIN A THIRD DIGITAL VIDEO STREAM OR RIGHT DIGITAL VIDEO STREAM FOR THE RIGHT EYE AND/OR SAID LEFT CORRECTION SCHEME TO AT LEAST A SECOND VIDEO FRAME OF SAID SECOND DIGITAL VIDEO STREAM SO AS TO OBTAIN A FOURTH DIGITAL VIDEO STREAM OR LEFT DIGITAL VIDEO STREAM FOR THE LEFT EYE

GENERATING A MULTIVIEW DIGITAL VIDEO STREAM COMPRISING A FIRST SUCCESSION OF VIDEO FRAMES ASSOCIATED TO SAID SECOND DIGITAL VIDEO STREAM OR SAID RIGHT DIGITAL VIDEO STREM AND A SECOND SUCCESSION OF VIDEO FRAMES ASSOCIATED TO SAID SECOND DIGITAL VIDEO STREAM OR TO SAID LEFT DIGITAL VIDEO STREAM

DISPLAYING SAID MULTIVIEW DIGITAL VIDEO STREAM BY MEANS OF A STEREOSCOPIC VIDEO SYSTEM IN SUCH A WAY THAT SAID FIRST SUCCESSION OF VIDEO FRAMES OF SAID MULTIVIEW DIGITAL VIDEO STREAM BE SEEN BY THE RIGHT EYE AND THAT SAID SECOND SUCCESSION OF VIDEO FRAMES OF SAID MULTIVIEW DIGITAL STREAM BE SEEN BY THE LEFT EYE

Fig. 2B

METHOD FOR MODIFYING AT LEAST ONE FRAME VIDEO OF A DIGITAL VIDEO STREAM TO BE DISPLAYED ON A DISPLAYING AREA AND RELATED SYSTEM

The present invention relates to a method and a relative system for modifying at least one video frame of a digital video stream to be displayed on a display area.

In particular, using this method, one or more digital video frames of said video stream are modified and coded to be displayed on a display area of a stereoscopic or autostereoscopic video system so that the contents of such video frames is perceived, by a person suffering from a degenerative disease of the retina (watching that display area), as correct or less affected by defects.

Using that method, the perception of visual defects, that a person suffering from said retinal degenerative disease may have in watching an image on a display surface, can be prevented and/or mitigated by changing that image and, therefore, the binocular vision of a person suffering from such a retinal degenerative disease is improved.

What we see is the visual perception of what we observe, that is, a resulting mental representation of the brain's elaboration, precisely in the visual cortex, of the signals coming from the eyes. These signals derive from the conversion of light stimuli into electrical impulses. This conversion is made by light-sensitive nerve cells (cone and rod cells) that form a retina layer. In other words, the eyes act as sensors wherein cone and rod cells work as photoreceptors.

An eye disease that somehow compromises its functioning can cause generation and transmission of altered signals to the brain.

In some particular cases, the merging process of the signals coming from the two eyes, effected by the cerebral cortex, can detect any anomalies and compensate for a proper binocular visual perception. When this is not possible, eye disease causes an incorrect visual perception.

In the latter case, therapeutic or non-therapeutic remedies can be made.

A therapeutic approach relates to procedures that act on the cause of the visual disorder.

For example, a drug or surgery may eliminate the defect in the eye. By using this medication or surgical procedure, it is possible to treat and heal the subject affected by the disease.

A non-therapeutic approach may include visual aids that, limited to the period of their use, can attenuate or eliminate completely the perception of visual defects without, however, intervening on the physiological causes of such visual defects.

This type of approach does not act on the person (i.e. on the organic causes) but on what the person sees.

In this context, the method (and the related system) subject-matter of the invention is introduced, since one or more video frames of a digital video stream referring to any visual content of interest (such as an image, in particular a photograph, or a television broadcast or a live video or a recorded video or a video output of a computer) displayed on a display area are modified to compensate for visual defects perceived by a subject suffering from a degenerative retinal disease, so that the visual perception of the subject is improved.

In other words, the method acts on one or more video frames reproduced on a display area and observed by said subject suffering from a degenerative retinal disease.

Consequently, the method of the invention has no influence on the retinal degenerative pathology and does not in any way alter the state of health of the subject in relation to said degenerative retinal disease and is therefore not a therapeutic method.

The subject remains affected by a degenerative retinal disease and the severity of such retinal degenerative pathology does not change with the application of the method.

The retinal degenerative pathologies are widespread and constantly increasing, especially for people over 50 years of age.

The retinal degenerative pathologies can cause serious and disabling visual defects for a person.

In general, degenerative retinal disorders cause degeneration of one or more areas of the retina and in particular of the macula, i.e. the retinal area responsible for the central vision and the ability to distinguish the details.

By simplifyingly, it is possible to imagine the retina as a membrane, disposed within a spherical shell, on which a plurality of cells is predisposed to the photoreceptor function.

The degeneration of the retina can result in an alteration in the shape of the membrane and hence an alteration in the disposition and orientation of the above cells. As a result, the image that is reconstructed by the brain, based on signals received from said cells, may be perceived distorted in the membrane areas in which the latter has assumed a curvature different from the normal one.

The effects may be different and more or less serious.

For example, if a focus is kept on a grid at the junction between a vertical line and a horizontal line (the so-called Amsler test), a healthy person sees rightly this point and also correctly perceives the rest of that grid, arranged around that point, included in its own field of view.

Unlike a healthy person, a person suffering from a degenerative retinal disease may have several visual defects. For example, he/she can see at least one portion of image as distorted (more or less accentuated) or he/she can see at least one image portion as blurred.

If the retinal degeneration is particularly severe, the perceived image may even be deprived of one or more portions (loss of partial visual information).

If the retinal degeneration affects only one eye, the most immediate possibility for carrying out most of the activity is the occlusion of that eye.

It is clear that this may be useless when both eyes are affected by a degenerative retinal disease. Some remedies for degenerative diseases are based on a surgical procedure.

For example, in some cases, it is possible to intervene with a laser to block the growth of abnormal blood vessels which cause swelling and consequently a deformation of the retina.

However, surgery may be risky, considering that patients are often elderly.

In other cases, where retinal degeneration can be caused by filamentous structures that act so as to raise and deform the retina layers, medication can be used, for example by injecting an enzyme that digests these filaments.

The remedies mentioned above are invasive remedies (especially those based on a surgery) and generally have a reduced success rate. In addition, remedies are more destined to blocking the progression of the disease rather than restoring a proper binocular vision.

In less severe cases, it is possible to reduce the perception of visual defects or improve binocular vision by using optical technologies. For example, through prismatic lenses, one can move an image of the scene that is observed in areas of the retina that are healthy, i.e. without any degenerative pathology.

The principle used is based on the brain's ability to correct or compensate, within certain limits, a misalignment between the images that come from the two eyes.

Additionally, to improve binocular vision, you can use different devices configured to enlarge an image, such as magnifiers or projectors. Such devices help improve binocular vision and are useful for a person for some daily activities, such as reading.

A known method for correcting macular distortion is described in U.S. Pat. No. 8,708,495.

The patent refers to a computerized system that allows a patient to visualize and modify the Amsler grid by moving the nodes of said Amsler grid according to his/her perception of the image.

The system calculates the vector field of displacements with a predetermined resolution by means of a two-dimensional interpolation scheme based on the displacements of said nodes. At this point, the images, that it receives as input, can be edited before being displayed, by applying predetermined shifts to them so to deform such images in such a way that the patient perceives them as correct.

A disadvantage of this system is that a patient may be disturbed by a part of the frame of the Amsler grid test, although that part doesn't fall into a retinal area subjected to deformation.

A further disadvantage is that the area of the deformation retina is identified with a fixed resolution.

A method and a known device for improving vision in subjects with a retinal disease are described in US patent application 2014/0210970.

In this patent application, one refers to a disease of the retina that can impair central vision and have glasses or headsets for virtual reality or augmented reality.

The method consists in the possibility to correct a defect degeneration by moving a portion of the image in the healthy parts of the retina, essentially arranged around the perimeter of the retina itself.

However, even this method of known type has disadvantages.

A disadvantage is the fact that the method is based on the brain's ability to correct or compensate for misalignment between the two images that are received from their eyes.

However, the brain cannot compensate for any misalignment, therefore there is a risk that a person sees a double image or that the image itself is subject to dynamic effects, such as flicker.

Another disadvantage is that the image processing requires considerable memory and remarkable execution speed to prevent the scene observed by a person loses fluidity, due to the dynamic range of the scene itself. As a result, fast movements within a scene or fast passages from one scene to the next scene may be lost.

Consequently, it is necessary to create a specific hardware to mount on spectacles or headsets, with the costs incurred to make the hardware and glasses or headsets.

The object of the present invention is to overcome those disadvantages by providing a method for modifying one or more video frames of a digital video stream and rendering it compatible with a stereoscopic or autostereoscopic video system so that it is displayed on a display area of said stereoscopic or autostereoscopic system, thus eliminating and/or reducing the perception of visual defects in a subject suffering from a degenerative retinal disease when said subject looks at said digital video stream on said display area.

Advantageously, the binocular vision of that subject while watching digital video flow is improved.

In particular, on the one hand, it is possible to eliminate the perception of visual defects caused by one or more alterations at one or more areas of the retina of an eye or both eyes when the degenerative retinal disease does not cause a loss of visual information.

On the other hand, it is possible to reduce the perception of such visual defects, when such alterations cause a loss of visual information.

This was achieved by a non-therapeutic method that allows two digital video streams, distinct from each other, to be generated from a digital video stream related to any visual content (such as a photograph, television broadcast, or live video), wherein each of said two digital video streams is intended for a respective eye and allows for correction schemes to be applied to at least one of said two digital video streams to modify the respective digital video stream so that the person suffering from degenerative pathology of the retina may have an improved visual perception or correct binocular vision.

It is therefore an object of the invention to modify one or more video frames of a digital video stream to be displayed on a display area, wherein a first eye reference system or right eye reference system is associated with the right eye, said right eye reference system being a three-dimensional Cartesian reference system, integral with the eyeball of the right eye, having an origin in the center of the cornea of said right eye and comprising a first axis, a second axis and a third axis, wherein said second axis is orthogonal to an interpupillary axis, wherein said interpupillary axis is a straight line passing through the center of the right eye cornea and the center of the left eye cornea, and said third axis coincides with a first visual axis, wherein said first visual axis is a straight line for the center of the right eye cornea and through an eye fixation point wherein said eye fixation point is a point of said display area observed by a person, said display area being part of a stereoscopic or autostereoscopic video system, a second eye reference system or left eye reference system is associated with the left eye, said left eye reference system being a three-dimensional Cartesian reference system, integral with the eyeball of said left eye, having an origin in the center of the cornea of said left eye and comprising a first axis, a second axis and a third axis, wherein said second axis is orthogonal to said interpupillary axis and said third axis coincides with a second visual axis, said second visual axis being a line passing through the center of the cornea of said left eye and through said eye fixation point, a display reference system is bound to the display area, said display reference system being a three-dimensional Cartesian coordinate system, having an origin in the center of the display area and comprising a first axis, a second axis, and a third axis, wherein said first axis is horizontal and said third axis is perpendicular to a display plane, wherein said display plane is a plane passing through said display area and arranged so that the display area belongs to the display plane.

In particular, said method comprises the following steps:

A) acquiring a first digital video stream, where said first digital video stream comprises a succession of first video frames;

B) individuating with respect to said first digital video stream, for the right eye, the shape, size and position of at least one first portion of video frame of at least one first video frame for which at least one first visual defect is perceived by said person, wherein the shape, size and position of said at least one first portion of a video frame is determined when said right eye reference system has the origin in a predetermined first position and a predetermined first orientation so that the following predetermined first conditions are satisfied:

said eye fixation point coincides with the center of said display area, said right eye is at a predetermined first distance from said display area, and said first axis and said second axis of said right eye reference system are parallel respectively to said first axis and said second axis of said display reference system;

and/or for the left eye, the shape, size and position of at least one second portion of video frame of at least one first video frame at which at least one second visual defect is perceived by said person, wherein the shape, size and position of said at least one second portion of video frame are determined when said left eye reference system has the origin in a predetermined second position and a predetermined second orientation such that the following predetermined second conditions are satisfied:

said eye fixation point coincides with the center of said display area, said left eye is at a predetermined second distance from said display area, and said first axis and said second axis of said right eye reference system are parallel respectively to said first axis and said second axis of said display reference system;

C) determining for said at least one first portion of video frame of said at least one first video frame, one or more first digital filters configured to modify the value of one or more pixels of said at least one first portion of video frame, each of which is associated with a respective predetermined first portion of video frame, and/or for said at least one second portion of video frame of said at least one first video frame, one or more digital filters configured to modify the value of one or more pixels of said at least one second portion of video frame, each of which is associated with a respective predetermined second portion of video frame;

D) configuring for the right eye, a first correction scheme or right correction scheme comprising said one or more first digital filters, wherein said right correction scheme is a first data structure configured to modify said at least one first portion of video frame, wherein said first data structure comprises information relating to said one or more first digital filters, information relating to said shape, said size and position of each of said first portions of video frame, and information relating to the associations of said first portions of video frame to each of said first digital filters; said right correction scheme having a graphic format so as to be displayed with a predetermined first image, wherein one or more portions of said predetermined first image are associated with a respective first digital filter and each first digital filter is associated with a respective predetermined first portion of video frame, and/or for the left eye, a second correction scheme or left correction scheme comprising one or more second digital filters, wherein said left correction scheme is a second data structure configured to modify said at least one second portion of video frame, wherein said second data structure comprises information relating to said one or more second digital filters, information relating to said shape, said size and position of each of said second portions of video frame, and information relating to the associations of said second portions of video frame to each of said second digital filters; said left correction scheme having a graphic format so as to be displayed with a predetermined second image, wherein one or more portions of said predetermined second image are associated with a respective second digital filter and each second digital filter is associated with a respective predetermined first portion of video frame;

E) acquiring a second digital video stream, wherein said second digital video stream comprises a succession of second video frames, said second video frames of said second digital stream being video frames referenced to a visual content that can be displayed on said display area;

F) calculating for said right eye a first position of the origin and a first orientation of said right eye reference system relative to said display reference system, and/or for said left eye, a second position of the origin and a second orientation of said left eye reference system with respect to said display reference system;

G) comparing with reference to said right eye, the first position of the origin of said right eye reference system with said predetermined first position of the origin in the predetermined first conditions to verify whether said first position of the origin of said right eye reference system is different from said predetermined first position and/or said first orientation of said right eye reference system with said predetermined first orientation in the predetermined first conditions to verify whether said first orientation is different from said predetermined first orientation and/or with reference to said left eye, the second position of the origin of said left eye reference system with the predetermined second position of the origin in the predetermined second conditions to verify if said second position of the origin is different from said predetermined second position and/or the second orientation of said left eye reference system with said predetermined second orientation in the predetermined second conditions to verify whether said second orientation is different from said predetermined second orientation;

H) when said first position of the origin of said right eye reference system is different from said predetermined first position of the origin and/or said first orientation of said right eye reference system is different from said predetermined first orientation, reconfiguring said right correction scheme based on said first position of the origin and/or said first orientation, such that said one or more first digital filters are applied to respective first portions of video frame, different from said predetermined first portions of video frame, and/or when said second position of the origin of said left eye reference system is different from said predetermined second position of the origin and/or said second orientation is different from said predetermined second orientation, reconfiguring said left correction scheme according to said second position of the origin and/or said second orientation, so that one or more second digital filters are applied to one or more respective second portions of video frame, different from said predetermined second portions of video frame;

I) applying said right correction scheme to at least one second video frame of said second digital video stream so that one or more first digital filters are applied to at least one first portion of video frame so as to obtain a third digital video stream or right digital stream for the right eye, different from said second digital video stream, wherein said right digital stream comprises at least one second modified video frame, and/or said left correction scheme to at least one second video frame of said second digital video stream so that said one or more second digital filters are applied to at least one second portion of video frame so as to obtain a fourth digital video stream or left digital stream for the left eye, different from said second digital video stream, wherein said left digital stream comprises at least one further second modified video frame;

L) generating a multiview digital video stream comprising a first sequence of video frames associated with said second digital video stream or said right digital video stream, and a second succession of video frames associated with said second digital video stream or said left digital video stream;

M) displaying said multiview digital video stream by said stereoscopic or autostereoscopic video system so that said first sequence of video frames of said multiview digital video stream is viewed from said right eye and said second succession of video frames of said multiview digital stream is seen from that left eye.

When said right eye and/or said left eye move and/or the head of said person moves, said method may further comprise the following steps:

F) calculating for said right eye a further first position of the origin and a further first orientation of said right eye reference system relative to said display reference system, and/or for said left eye, a further second position of the origin and a further second orientation of said left eye reference system with respect to said display reference system;

G1) comparing said further first position of the origin of said right eye reference system with said predetermined first position of the origin in the predetermined first conditions to verify whether said further first position of the origin of said right eye reference system is different from said predetermined first position and/or said further first orientation of said right eye reference system with said predetermined first orientation in the predetermined first conditions to verify whether said further first orientation is different from said predetermined first orientation and/or said further second position of the origin of said left eye reference system with said predetermined second position of the origin in the predetermined second conditions to verify if said further second position of the origin is different from said predetermined second position and/or said further second orientation of said left eye reference system with said predetermined second orientation in the predetermined second conditions to verify whether said further second orientation is different from said predetermined second orientation;

G2) for said right eye comparing said further first position of the origin of said right eye reference system with said first position to verify whether said further first position of the origin is different from said first position of the origin when said further first position of the origin of said right eye reference system is different from said predetermined first position of the origin in the predetermined first conditions, and/or said further first orientation of said right eye reference system with said first orientation to verify whether said further first orientation is different from said first orientation, when said further first orientation of said right eye reference system is different from said predetermined first orientation in the predetermined first conditions, and/or for said left eye comparing said further second position of the origin of said left eye reference system with said second position of the origin to verify whether said further second position of the origin is different from said second position of the origin, when said further second position of the origin of said left eye reference system is different from said predetermined second position of the origin in the predetermined second conditions, and/or said further second orientation of said left eye reference system with said second orientation to verify whether said further second orientation is different from said second orientation, when said further second orientation of said left eye reference system is different from said predetermined second orientation in the predetermined first conditions;

H') reconfiguring said right correction scheme according to said further first position of the origin as calculated, when said further first position of the origin of said right eye reference system is different from said first position of the origin and/or based on said further first calculated orientation, when said further first orientation is different from said first orientation, and/or reconfiguring said left correction scheme according to said further second origin position as calculated when said further second position of the origin of said left eye reference system is different from said second position of the origin and/or based on said further second orientation as calculated, when said further second orientation is different from said second orientation.

With reference to each of said first video frames, each of said first video frames may be an Amsler grid.

With reference to each first digital filter and each second digital filter, each first digital filter can be graphically represented in a respective portion of said predetermined first image of said right correction scheme and each second digital filter can be represented graphically in a respective further portion of said predetermined second image of said left correction scheme.

With reference to the visual content of the second digital video stream, such visual content may be an image or a television broadcast or a live video or a recorded video or a video output of a computer.

The present invention also relates to a system for modifying one or more video frames of a digital video stream displayable on a display area, said system comprising:

a second video source configured to provide a second digital video stream, wherein said second digital video stream comprises a succession of second video frames; said second video frames of said second digital stream being referred to a visual content displayable on said display area;

a tracking system for tracking an eye fixation point in the display area, configured at least to calculate:

for the right eye a first position of the origin and a first orientation of a right eye reference system with respect to a display reference system, said right eye reference system being a three-dimensional Cartesian reference system, integral with the eyeball of said right eye, having an origin in the center of the cornea of said right eye and comprising a first axis, a second axis and a third axis, wherein said second axis is orthogonal to an interpupillary axis, wherein said interpupillary axis is a straight line through the center of the cornea of the right eye and the center of the cornea of the left eye, and said third axis coincides with a first visual axis, wherein said first visual axis is a straight line passing through the center of the right eye cornea and said eye fixation point, a display reference system is associated with said display area, said display reference system being a three-dimensional Cartesian reference system having an origin in the center of said display area and comprising a first axis, a second axis, and a third axis, wherein said first axis is horizontal and said third axis is perpendicular to a display plane, wherein said display plane is a plane passing through said display area arranged such that said display area belongs to said display plane, and/or for the left eye, a second position of the origin and a second orientation of said left eye reference system relative to said display reference system, said left eye reference system being a three-dimensional Cartesian reference system, integral with the eyeball of said left eye, having an origin in the center of the cornea of said left eye and comprising a first axis, a second axis and a third axis, wherein said second axis is orthogonal to said interpupillary axis and said third axis coincides with a second visual axis, wherein said second visual axis is a straight line through the center of the cornea of said left eye and through said eye fixation point;

a correction device adapted to modify the video frames of a digital video stream on the basis of visual defects perceived due to a degenerative retinal disease in which a first correction scheme or right correction scheme is stored, comprising one or more first digital filters configured to modify the value of one or more pixels of at least one first portion of video frame, wherein each first digital filter is associated with at least one predetermined first portion of video frame, and/or a second correction scheme or left correction scheme comprising one or more second digital filters configured to modify the value of one or more pixels of at least one second portion of video frame, wherein each second digital filter is associated with at least one predetermined second portion of video frame, said right correction scheme being a first data structure including information relating to said one or more first digital filters, information relating to the shape, size, and position of at least one first portion of video frame at which at least one first visual defect is perceived by a person, and information relating to the associations of said first portions of video frame to each of said first digital filters; said right correction scheme having a graphic format so as to be displayed with a predetermined first image, wherein one or more portions of said predetermined first image are associated with a respective first digital filter and each first digital filter is associated with a respective predetermined first portion of video frame, said left correction scheme being a second data structure comprising information relating to said one or more second digital filters, information relating to shape, size, and position of at least one second portion of video frame at which at least one second visual defect is perceived by a person, and information relating to the associations of said second portions of video frame to each of said second digital filters; said left correction scheme being a second data structure comprising information relating to said one or more digital filters, information relating to shape, size and position of at least one second portion of video frame at which at least one second visual defect is perceived by a person, and information relating to the associations of said second portions of video frame to each of second digital filters; said left correction scheme having a graphic format so as to be displayed with a predetermined second image, wherein one or more portions of said predetermined second image are associated to a respective second digital filter and each second digital filter is associated to a respective predetermined second portion of video frame;

a stereoscopic or autostereoscopic video system, wherein said stereoscopic or autostereoscopic video system comprises a display device provided with said display area.

In particular, said correction device is connected to said second video source as well as to said tracking system and to said stereoscopic or autostereoscopic video system and is configured at least for:

acquiring said second digital video stream, wherein said second digital video stream comprises a succession of second video frames;

receiving from said tracking system with reference to said right eye, said first position of the origin and/or said first orientation of said right eye reference system, and/or with reference to said left eye, said second position of the origin and/or said second orientation of a left eye reference system;

comparing with reference to said right eye, said first position of the origin of said right eye reference system with a predetermined first position of the origin to verify whether said first position of the origin is different from said predetermined first position, and/or said first orientation of said right eye reference system with a predetermined first orientation to verify whether said first orientation is different from said predetermined first orientation, said predetermined first position of the origin and said predetermined first orientation being such that the following predetermined first conditions are satisfied:

said eye fixation point coincides with the center of said display area, said right eye is at a predetermined first distance from said display area, and said first axis and said second axis of said right eye reference system are parallel respectively to said first axis and said second axis of said display reference system;

and/or with reference to said left eye, said second position of the origin of said left eye reference system with a predetermined second position of the origin to verify whether said second position of the origin is different from said predetermined second position and/or said second orientation of said left eye reference system with a predetermined second orientation to verify whether said second orientation is different from said predetermined second orientation, said predetermined second position of the origin and said predetermined second orientation being such that the following predetermined second conditions are satisfied:

said eye fixation point coincides with the center of said display area, said left eye is at a predetermined second distance from said display area, and said first axis and said second axis of said left eye reference system are parallel respectively to said first axis and said second axis of said display reference system;

reconfiguring said right correction scheme according to said first position of the origin and/or said first orientation so that said one or more first digital filters are applied to respective first portions of video frame different from said predetermined first portions of video frame, when said first position of the origin of said right eye reference system is different from said predetermined first position of the origin and/or said first orientation of said right eye reference system is different from said predetermined first orientation and/or reconfiguring said left correction scheme according to said second position of the origin and/or said second orientation so that one or more second digital filters are applied to one or more respective second portions of video frame different from said predetermined second portions of video frame, when said second position of the origin of said left eye reference system is different from said predetermined second position of the origin and/or said second orientation is different from said predetermined second orientation;

applying said right correction scheme to at least one second video frame of said second digital video stream so that one or more first digital filters are applied to at least one first portion of video frame so as to obtain a third digital video stream or right digital stream for the right eye, different from said second digital video stream, wherein said right digital stream comprises at least one second modified video frame, and/or said left correction scheme to at least one second video frame of said second digital video stream so that said one or more second digital filters are applied to at least one second portion of video frame so as to obtain a fourth digital video stream or left digital stream for the left eye, different from said second digital video stream, wherein said left digital stream comprises at least one further second modified video frame;

generating a multiview digital video stream comprising a first sequence of video frames associated with said second digital video stream or said right digital video stream, and a second succession of video frames associated with said second digital video stream or said left digital video stream;

performing a video coding compatible with said stereoscopic or autostereoscopic video system;

said stereoscopic or autostereoscopic video system is configured to:

receive said multiview digital video stream, display said multiview digital video stream so that said first sequence of video frames of said multiview digital video stream is viewed from said right eye and said second succession of video frames of said multiview digital stream is seen from that left eye.

With reference to the right correction scheme and the left correction scheme, said right correction scheme may include a plurality of first digital filters, and said left correction scheme may include a plurality of said second digital filters.

With reference to each first digital filter and each second digital filter, each first digital filter can be graphically represented in a respective portion of said predetermined first image of said right correction scheme and each second digital filter can be represented graphically in a respective further portion of said predetermined second image of said left correction scheme.

In a variation, said system may comprise a first digital video source configured to provide a first digital video stream comprising a succession of first video frames, in respect of which said one or more digital filters and/or said one or more second digital filters are determined. In this variation, said correction device is connected to said first video source.

In particular, said first video source may be said second video source, so that said system has only one video source.

Similarly to the method, with reference to the system, said visual content of said second digital video stream may be a frame or a television broadcast or a live video or a recorded video or a video output of a computer.

The present invention will now be described, by way of illustration, but not by way of limitation, according to one embodiment, with particular reference to the accompanying drawings, in which:

FIG. 1 schematically shows both the system and the method of the invention;

FIG. 2 (split into FIGS. 2A and 2B) shows a flow diagram of the method for modifying one or more video frames of a digital video stream that is displayed on a display area according to the invention;

FIG. 3A schematically shows the right eye that looks at a display area as well as a first correction scheme for modifying at least one video frame portion of a digital video stream based on the visual defects of the right eye, and the eye fixation point which coincides with the origin of the display reference system associated with the display area;

FIG. 3B schematically shows the left eye looking at a display area as well as a second correction scheme for modifying at least one video frame portion of a digital video stream based on visual defects of said left eye, and the eye fixation point coincides with the origin of the display reference system associated with the display area;

FIG. 4 schematically illustrates the situation in which, with reference to the right eye, the eye fixation point has shifted from the original position and is at a point different from the origin of the display reference system and a rototranslation has been applied to the first correction scheme;

FIG. 5 shows the situation in which said first rototranslated correction scheme has been projected on a display plane passing through the display area according to the direction of the first visual axis and a first image including the points of the display plane included in the display area;

FIG. 6 schematically shows the situation where, with reference to the left eye, the eye fixation point has moved from the original position and is at a different point from the origin of the display reference system and a rototranslation to the second correction scheme has been applied;

Figure 8:
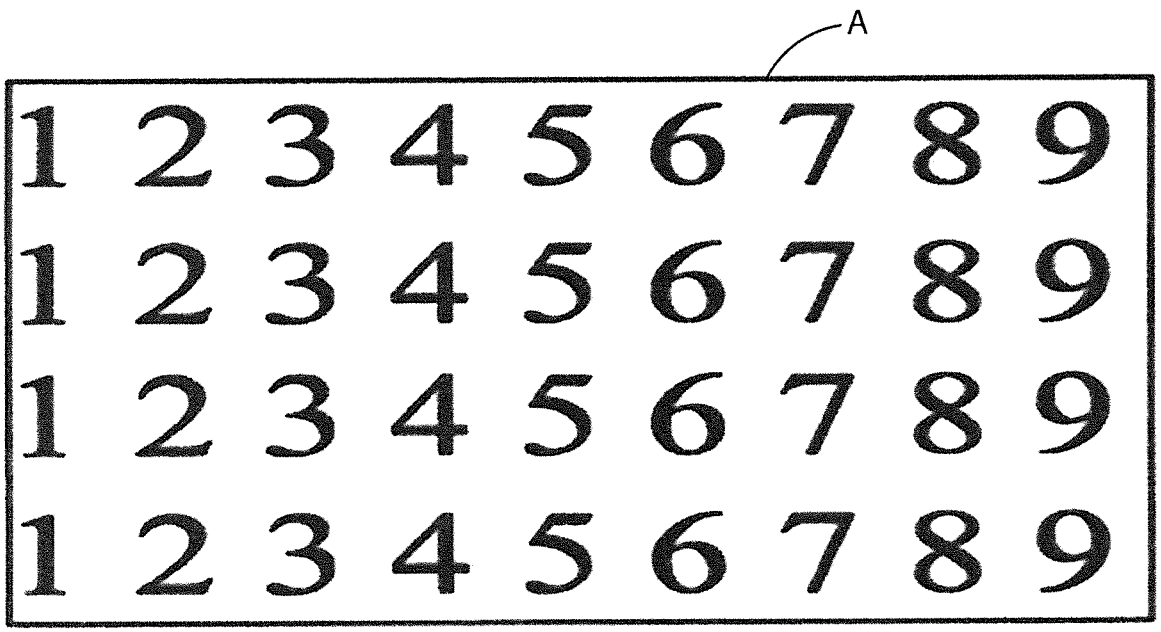
FIG. 8 shows an image provided by a video origin and displayed on a display area.
Figure 11A:
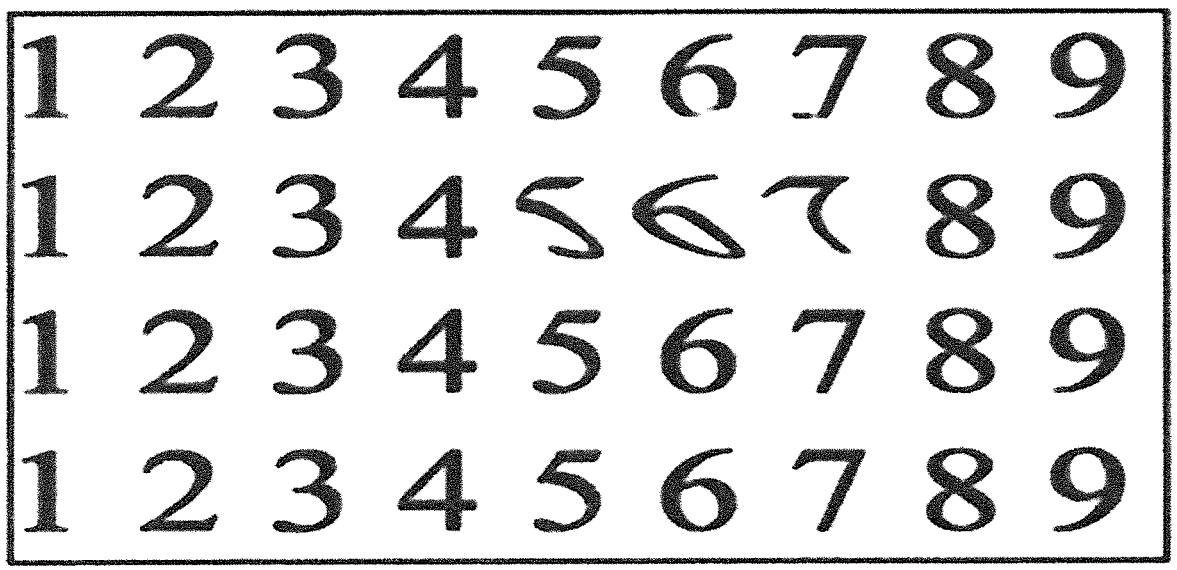
Figure 11B:
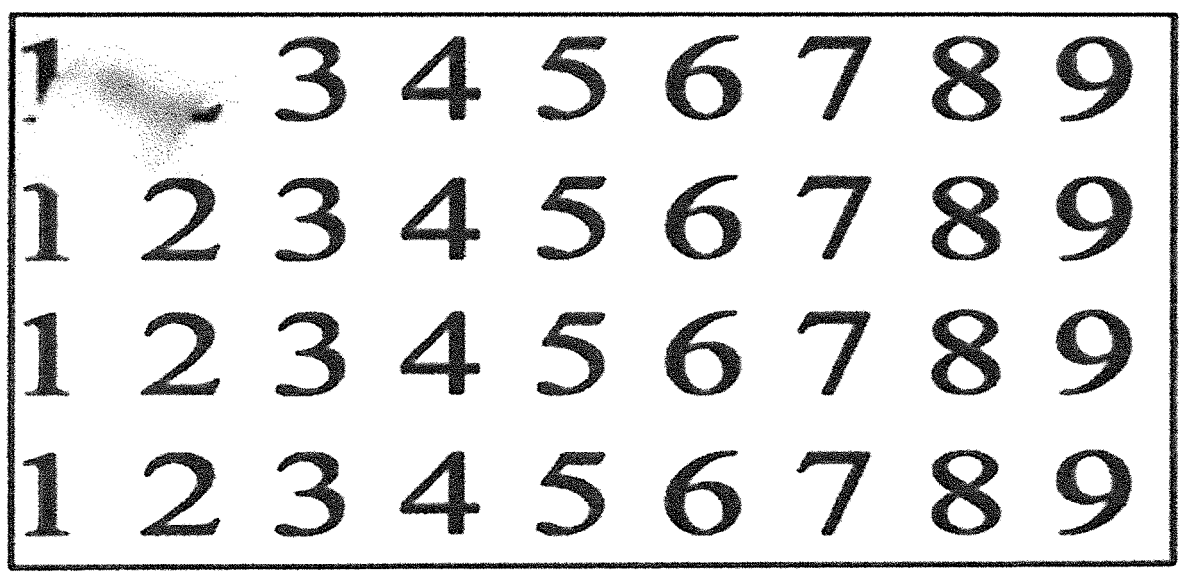
Figure 12A:
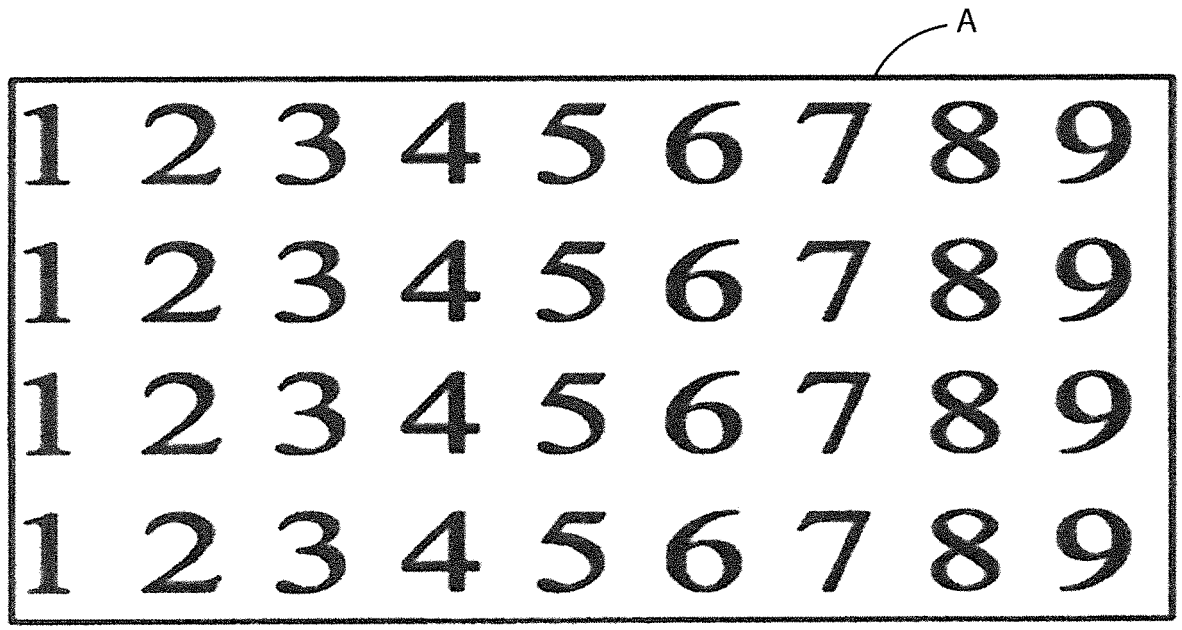
Figure 12B:
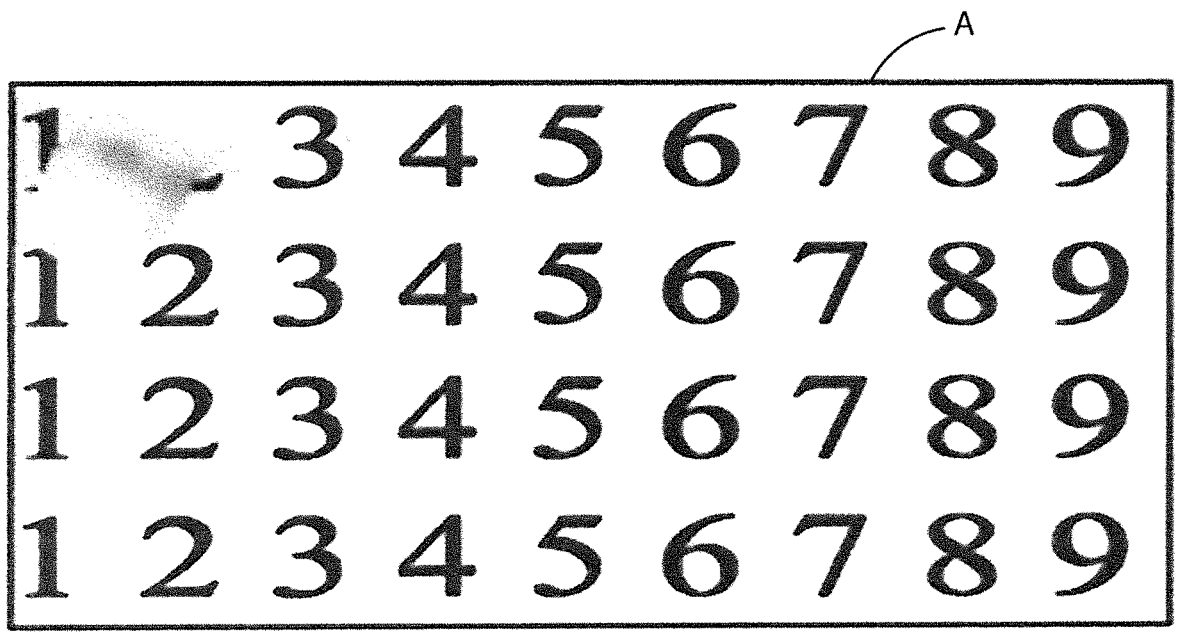
Figure 12C:
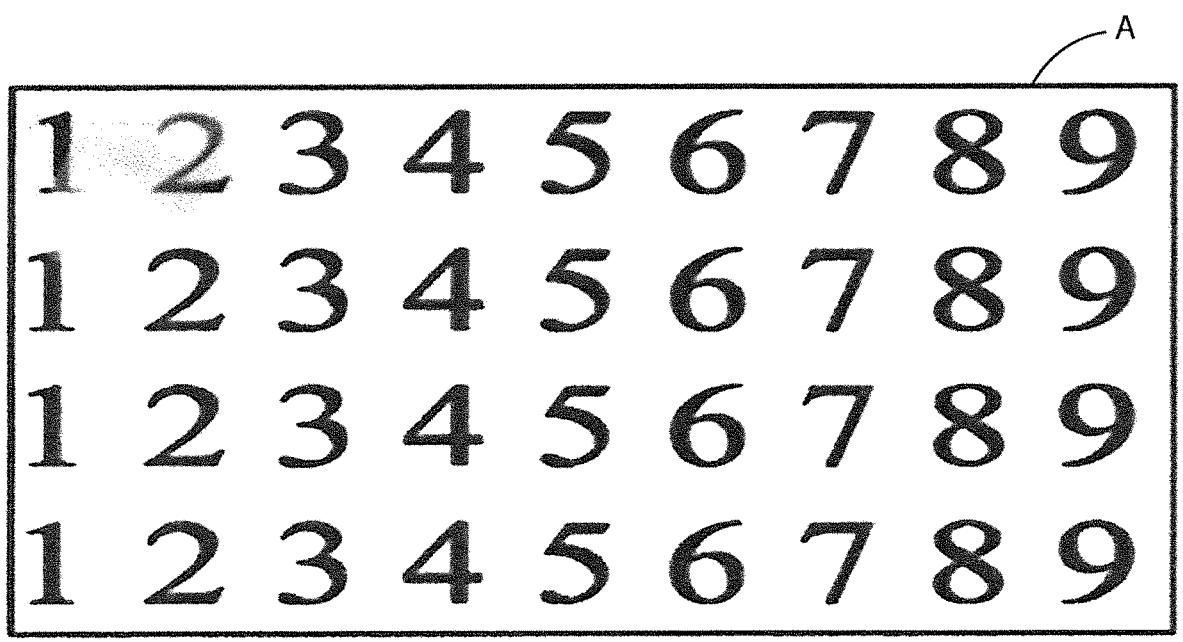

FIGS. 11A and 11B respectively show the effect of the first digital filter of the first correction scheme and the effect of the second digital filter of the second correction scheme;

FIGS. 12A and 12B respectively show the perceived image after applying the first correction scheme and the perceived image after the application of the second correction scheme when a person suffering from a degenerative retinal disease looks at the center of said image with the only right eye and with the only left eye;

FIG. 12C shows the frame of FIG. 8 as it would be perceived by a person suffering from a degenerative retinal disease that looks at the center of said image with both eyes.

With reference to the figures, a method for modifying one or more video frames of a digital video stream that is displayed on a display area is shown.

Before entering the merit of the method, it should be stated that:

Video source means any electronic device capable of providing a digital video stream comprising a plurality of video frames, such as cameras or computers or receiving means for receiving television signals; in other words, video source means a digital video source;

Digital video stream means a succession of digital video frames;

A display area is an area for displaying a digital video stream, such as the area of a television screen or computer monitor;

Display plane means a plane passing through the display area arranged so that said display area belongs to said display plane, i.e. the plane to which said display area belongs;

Eye fixation point means the point of the display area that is observed by a user at a given instant;

First visual axis is a straight line through the center of the cornea of the right eye and through the eye fixation point;

Second visual axis is a straight line through the center of left eye cornea and for through eye fixation point;

Interpupillary axis is a straight line through the center of the right eye's cornea and through the center of the left eye cornea;

Display reference system is a three-dimensional Cartesian reference system having an origin O in the center of said display area and comprising a first axis x, a second axis y, and a third axis z, wherein said first axis x is horizontal and said third axis z is perpendicular to the display plane;

The first eye reference system or right eye reference system means a three-dimensional Cartesian reference system, integral with the right eye bulb, having an origin $O_1$ in the center of the cornea of said right eye and comprising a first axis $x_1$, a second axis $y_1$ and a third axis $z_1$, wherein said second axis $y_1$ is orthogonal to said interpupillary axis and said third axis $z_1$ coincides with said first visual axis;

The second eye reference system or left eye reference system refers to a three-dimensional Cartesian reference system, integral to the left eye bulb, having an origin $O_2$ in the center of the cornea of said left eye and comprising a first axis $x_2$, a second axis $y_2$ and a third axis $z_2$, wherein said second axis $y_2$ is orthogonal to said interpupillary axis and said third axis $z_2$ coincides with said second visual axis;

The first digital filter is meant as a first sequence of operations on one or more pixels configured to modify the value of said one or more pixels of at least one first portion of video frame of a digital video stream according to a predetermined first algorithm, such as an algorithm for varying the brightness or algorithm for varying one or more levels of gray or an algorithm for introducing a blur effect or a distorting effect;

Second digital filter means a second sequence of operations on one or more pixels configured to modify the value of said one or more pixels of at least one second portion of video frame of a digital video stream according to a predetermined second algorithm, such as an algorithm for varying the brightness or algorithm for varying one or more levels of gray or an algorithm for introducing a blur effect or a distorting effect;

The first correction scheme or right correction scheme is meant a first data structure configured to modify said at least one first portion of video frame of a digital video stream based on visual defects in the right eye, Wherein said first data structure comprises information relating to one or more first digital filters, information relating to the shape, size and position of each of said first portions of video frame relative to the display reference system, and information relating to the association of said first portions of video frame to each of said first digital filters, wherein the shape, size, and position of each of said first portions of video frame are detected when said right eye reference system has the origin $O_1$ at a predetermined first position and a predetermined first orientation such to meet the following predetermined first conditions:

The eye fixation point coincides with the center of the display area,

Said right eye is at a predetermined first distance from said display area, and

The first axis $x_1$ and the second axis $y_1$ of said right eye reference system are parallel to the first axis x and to the second axis y of said display reference system, consequently the third axis $z_1$ of said right eye reference system is aligned with the third axis z of the display reference system;

Said right correction scheme having a graphic format so as to be displayed with a predetermined first image, one or more portions of said predetermined first image being associated with a respective first digital filter and each first digital filter being associated with a respective predetermined first portion of video frame;

With a second correction scheme or left correction scheme is meant a second data structure configured to modify said at least one second portion of video frame of a digital video stream based on visual defects in the eye, wherein said second data structure comprises information relating to one or more second digital filters, information about shape, size, and position of each of said second portions of video frame relative to the display reference system and information relating to the associations of said second portions of video frame to each of said second digital filters, wherein the shape, size, and position of each of said second portions of video frame are detected when said left eye reference system has the origin $O_2$ at a predetermined second position and a predetermined second orientation to meet the following predetermined second conditions:

The eye fixation point coincides with the center of the display area,

Said left eye is at a predetermined second distance from said display area, and

The first axis $x_2$ and the second axis $y_2$ of said second eye reference system are parallel to the first axis x and to the second axis y of said display reference system, consequently the third axis $z_2$ of said left eye reference system is aligned with the third axis z of the display reference system; said left correction scheme having a graphic format so as to be displayed with a predetermined second image, one or more portions of said predetermined second image being associated with a respective second digital filter and each second filter being associated with one or more predetermined second portions video frame;

Tracking system is a system for tracking the eye fixation point of each eye, configured to calculate a first position of the origin $O_1$ and a first orientation of the right eye reference system with respect to the display reference system, and a second position of the origin $O_2$ and a second orientation of the left eye reference system with respect to the display reference system;

Correction device means a device designed to modify video frames of a digital video stream based on visual defects caused by the retinal degenerative pathology, configured for:

acquiring a digital video stream, memorizing said right correction scheme and/or said left correction scheme, receiving from said tracking system With reference to said right eye, said first position of the origin $O_1$ and/or said first orientation of said right eye reference system, and/or With reference to said left eye, said second position of the origin $O_2$ and/or said second orientation of a left eye reference system;

verifying

If the first position of the origin $O_1$ and the first orientation of the right eye reference system are respectively different from the predetermined first position of the origin $O_1$ and from the predetermined first orientation of the right eye reference system in the predetermined first conditions, and/or If the second position of the origin $O_2$ and the second orientation of the left eye reference system are different from the predetermined second position of the origin $O_2$ and from the predetermined second orientation of the left eye reference system itself in the predetermined second conditions;

reconfiguring, with reference to the right eye reference system, the right correction scheme when the first position of the origin $O_1$ is different from the predetermined first position of the origin $O_1$ and/or when the first orientation is different from the predetermined first orientation, and/or reconfiguring, with reference to the left eye reference system, the left correction scheme when the second position of the origin $O_2$ is different from the predetermined second position of the origin $O_2$ and/or the second orientation is different from the predetermined second orientation, applying said right correction scheme to at least one video frame of said digital video stream, so as to modify one or more video frames of said digital video stream and generate a modified digital video stream for the right eye and/or said left correction scheme to at least one video frame of said digital video stream, so as to modify one or more video frames of said digital video stream and generate a further modified digital video stream for the left eye, and generating a multiview digital video stream comprising a first succession of video frames associated with said digital video stream or said modified digital video stream, wherein said first succession of video frames is destined to the right eye, and a second succession of video frames associated with said digital video stream or said further modified digital video stream, wherein said second succession of video frames is destined to the left eye, transmitting said multiview digital video stream to a stereoscopic or autostereoscopic video system, said multiview digital video stream being coded according to a predetermined video coding of a known type compatible with said stereoscopic or autostereoscopic video system;

Stereoscopic or autostereoscopic video system means any stereoscopic system (for example, a video system comprising a display device and glasses that may be passive or active in combination with said display device) or any autostereoscopic system (for example, a video system comprising an autostereoscopic display device) for reproducing a digital video stream over said display area, said stereoscopic or autostereoscopic video system having said display area and is configured to:

receiving said multiview digital video stream input, and visualizing said multiview digital video stream so that this first succession of video frames of said multiview digital video stream be seen by the right eye and the second succession of video frames of said multiview digital video stream be seen by the left eye.

Figure 1:
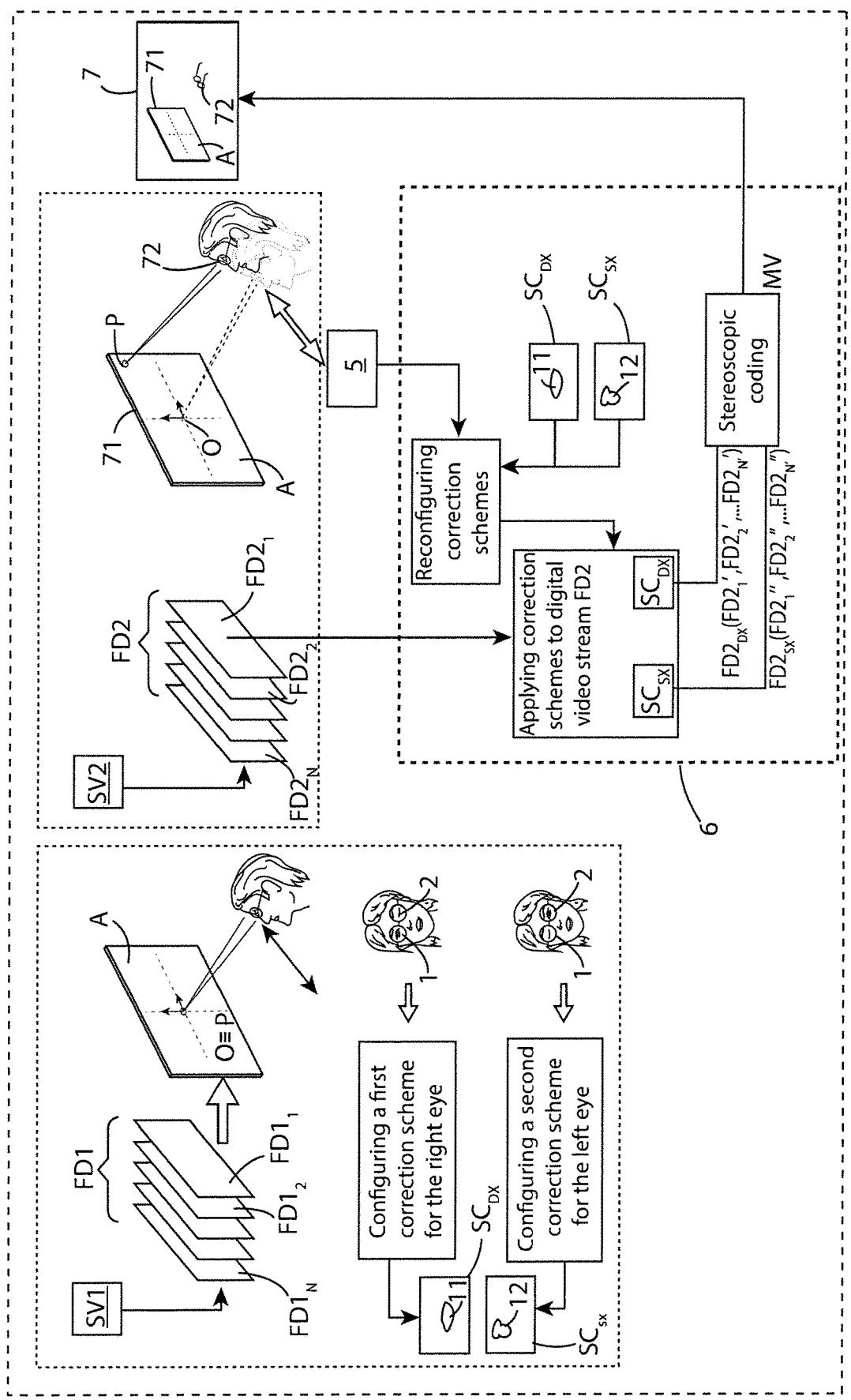

With reference to FIG. 1, both the system and the method subject matter of the invention is shown schematically, for modifying one or more digital video frames of a video stream in such a way as to correct and/or mitigate the perception of visual defects due to a degenerative disease.

In a first box of FIG. 1 (top left), a first digital video stream FD1, generated by a first video source SV1, comprising a plurality of first video frames $FD1_1, FD1_2 \ldots FD1_N$ and a person who looks at the display area A of a video system 7 are shown.

In the illustrated embodiment, said video system 7 is a stereoscopic video system, wherein said stereoscopic system comprises a display device 71 having said display area and a spectacle 72 compatible with said display device 71. In particular, the person is positioned at a predetermined distance from display area A and looks at a point of said display area A.

The point of display area A observed by said person is the eye fixation point and is indicated by reference P.

This point is first observed only with the right eye 1 (holding the left eye 2 closed), and then only with the left eye 2 (holding the right eye 1 closed).

When said point is observed only with the right eye 1, the right eye reference system has the origin $O_1$ at a predetermined first position and a predetermined first orientation such that the eye fixation point P coincides with the center of the display area A, the right eye is at a predetermined first distance D1 from the display area A and the first axis $x_1$ and the second axis $y_1$ of the first eye reference system are parallel to the first axis x and the second axis y of the display reference system respectively. As a result, the third axis $z_1$ of the first eye reference system is aligned to the third axis z of the display reference system.

When said point is observed only with the left eye 2, the left eye reference system has the origin $O_2$ at a predetermined second position and a predetermined second orientation such that the eye fixation point P coincides with the center of display area A, the left eye is at a predetermined second distance D2 from display area A and the first axis $x_2$ and the second axis $y_2$ of the second eye reference system are parallel to the first axis x and the second axis y of the display reference system. As a result, the third axis $z_2$ of the second eye reference system is aligned to the third axis z of the display reference system.

Thus, in these predetermined conditions, the following are identified:

The shape, the size and the position of at least one first portion of a video frame at which at least one first visual defect is perceived by a person who looks with the right eye, and The shape, the size, and the position of at least one second portion of video frame at which at least one second visual defect is perceived by a person looking with the left eye.

In these predetermined conditions, one or more first digital filters 11 are determined, each of which is associated with a respective first portion of video frame at which a first visual defect is perceived by a person, and one or more second digital filters 12, each of which is associated with a respective second portion of video frame at which a second visual defect is perceived by a person.

In the example that is described, the right eye 1 and the left eye 2 have respectively a first retinal area and a second retinal area with a respective degenerative pathology, so that a first visual defect is perceived by a person in correspondence of a first portion of video frame and a second visual defect is perceived by the same person at a second portion of video frame.

In the example described, a first digital filter 11 to be associated with a predetermined first portion of video frame and a second digital filter 12 to be associated with a predetermined second portion of video frame are determined.

Additionally, a first correction scheme or right correction scheme $SC_{DX}$ and a second correction scheme or left correction scheme $SC_{SX}$ are configured, each of which comprises respectively the first digital filter 11 and the second digital filter 12 respectively.

Graphically, each correction scheme $SC_{DX}$, $SC_{SX}$ has a graphic format and is then displayed with a respective predetermined image.

The predetermined first image with which said right correction scheme $SC_{DX}$ is displayed and the predetermined second image with which said left correction scheme $SC_{SX}$ is displayed are represented in FIG. 1 and each of them shows the respective digital filter to be applied to a respective portion of video frame.

In a second box of FIG. 1 (top right) a second video source SV2 is shown, which generates a second digital video stream FD2 (different from said first digital video stream FD1) comprising a plurality of second video frames $FD2_1$, $FD2_2$ ... $FD2_N$, and the same person who looks at a point of the display area A, different from the center of said display area A.

In particular, said second video frames $FD2_1$, $FD2_2$ ... $FD2_N$ of said second digital video stream FD2 are referred to a respective visual content that is displayed on said display area (for example said second digital video stream can be a movie, or a succession of images) and the person watching the display area A with both eyes, and the eye fixation point P is moved from a first position, in which it coincided with the center of the display area A (itself coinciding with the origin O of the display reference system), to a second position, in which it coincides with a peripheral point of the display area A, far from the center of the display area A.

The tracking system indicated by the reference numeral 5, respectively, calculates the position of the origin $O_1$ and the orientation of the first eye reference system and the second eye reference system, with respect to the display reference system.

A correction device 6 is connected to said second video source SV2, to said tracking system 5, as well as to said stereoscopic video system 7, and reconfigures said right correction scheme $SC_{DX}$ and said left correction scheme $SC_{SX}$, based on the position and/or the orientation of the respective eye reference systems, calculated by the tracking system 5.

Although a first video source SV1 and a second video source SV2 are shown in the figure and the correction device is connected to each of said video sources (although not shown), the presence of these two distinct video sources is not required.

In fact, with reference to the system subject-matter of the invention, only one video source which can provide both the first digital video stream FD1 and the second digital video stream FD2 is sufficient, and that the correction device is connected to said video source. Consequently, said second video source SV2 may coincide with the first video source SV1, without thereby departing from the scope of the invention.

Said correction device 6 applies said right correction scheme $SC_{DX}$ and said left correction scheme $SC_{SX}$ to at least one second video frame $FD2_1$, $FD2_2$ ... $FD2_N$ of the second digital video stream FD2.

When said correction device 6 applies said right correction scheme $SC_{DX}$ to said at least one second video frame $FD2_1$, $FD2_2$ ... $FD2_N$ of the second digital video stream FD2 is generated a third digital video stream or right digital flow $FD2_{DX}$, different from said second digital video stream FD2, comprising at least one second modified video frame $FD2_1'$, $FD2_2'$ ... $FD2_N'$.

When said correction device 6 applies said left correction scheme $SC_{SX}$ to at least one second video frame $FD2_1$, $FD2_2$ ... $FD2_N$ of the second digital video stream FD2, a fourth digital video stream or left digital stream $FD2_{SX}$ different from said second FD2 digital video stream is generated, which comprises at least one further second modified video frame $FD2_1''$, $FD2_2''$ ... $FD2_N''$.

In addition, the correction device 6 executes a video encoding (in this case a video encoding compatible with the stereoscopic video system 7) of said right digital video stream $FD2_{DX}$ (or of said second digital video stream FD2 in case no right correction scheme $SC_{DX}$ has been applied to a second video frame of said second digital video stream FD2) and said left digital video stream $FD2_{SX}$ (or of said second digital video stream FD2 in case no left correction scheme $SC_{SX}$ has been applied to a second video frame of said second digital video stream FD2) for generating a multiview digital video stream MV which comprises a first sequence of video frames associated with said right digital video stream $FD2_{DX}$ (or said second digital video stream FD2) and a second succession of video frames associated with said left digital video stream $FD2_{SX}$ (or said second digital video stream FD2) and transmits said multiview digital video stream to a stereoscopic video system 7, connected to said correction device. In this way, said first sequence of video frames associated with said right digital video stream $FD_{DX}$ (or said second digital video stream FD2) is seen by the right eye 1 and said second sequence of video frames associated with said left digital video stream $FD_{SX}$ (or said second digital video stream FD2) is seen by the left eye 2, and the content of the video frames of each sequence of video frames is seen by a respective eye in the most correct way possible.

Accordingly, the method of the invention comprises the following steps (FIG. 2):

A) acquiring a first digital video stream FD1, wherein said first digital video stream comprises a succession of first video frames $FD1_1$, $FD1_2$ ... $FD1_N$;

B) identifying from said first digital video stream FD1, for the right eye 1 the shape, size and position of at least one first portion of video frame of at least one first video frame $FD1_1, FD1_2 \ldots FD1_N$ in correspondence of which at least one first visual defect is perceived by a person, where the shape, the size and the position of said at least one first portion of video frame are determined when said right eye reference system has the origin $O_1$ in a predetermined first position and a predetermined first orientation such that the following predetermined first conditions are met:

the eye fixation point P coincides with the center of said display area A, the right eye 1 is at a predetermined first distance D1 from said display area A, and the first axis $x_1$ and the second axis $y_1$ of the first eye reference system are respectively parallel to the first axis x and the second axis y of the display reference system; and/or for the left eye 2 the shape, size and position of at least one second portion of video frame of at least one first video frame $FD1_1, FD1_2 \ldots FD1_N$ in correspondence of which a second visual defect is perceived by a person, where the shape, size and the position of said at least one second portion of video frame are determined when said left eye reference system has the origin $O_2$ in a predetermined second position and a predetermined second orientation such that the following predetermined second conditions are met:

the eye fixation point P coincides with the center of said display area A, the left eye 2 is at a predetermined second distance D2 from said display area A, and the first axis $x_2$ and the second axis $y_2$ of said second eye reference system are respectively parallel to the first axis x and the second axis y of said display reference system;

C) determining (with respect to said first digital video stream FD1), for said at least one first portion of video frame of said at least one first video frame $FD1_1, FD1_2 \ldots FD1_N$ one or more first digital filter 11 configured to change the value of one or more pixels of said at least one first portion of video frame, each of which is associated with a respective predetermined first portion of video frame, and/or for said at least one second portion of video frame of said at least one first frame video $FD1_1, FD1_2 \ldots FD1_N$ one or more second digital filters 12 configured to change the value of one or more pixels of said at least one second portion of video frame, each of which is associated with a respective predetermined second portion of video frame;

D) configuring:

for the right eye 1, a first correction scheme or right correction scheme $SC_{DX}$ comprising said one or more first digital filters 11, wherein said right correction scheme $SC_{DX}$ has a graphic format, so as to be displayed with a predetermined first image, and wherein a respective portion of said predetermined first image is associated with said at least one first portion of video frame, and/or for the left eye 2, a second correction scheme or left correction scheme $SC_{SX}$ comprising one or more second digital filters 12, wherein said left correction scheme $SC_{SX}$ has a graphic format, so as to be displayed with a predetermined second image, and wherein a respective portion of said predetermined second image is associated with said at least one second portion of video frame;

E) acquiring a second digital video stream FD2, wherein said second digital video stream FD2 comprises a succession of second video frames $FD2_1, FD2_2 \ldots FD2_N$;

F) calculating:

for the right eye 1, a first position of the origin $O_1$ and a first orientation of said right eye reference system with respect to said display reference system, and/or for the left eye 2, a second position of the origin $O_2$ and a second orientation of said left eye reference system with respect to said display reference system;

G) comparing the first position of the origin $O_1$ of said right eye reference system with said predetermined first position of the origin $O_1$ in the predetermined first conditions to verify if said first position of the origin $O_1$ is different from said predetermined first position and/or the first orientation of said right eye reference system with said predetermined first orientation in the predetermined first conditions for verifying whether said first orientation is different from said predetermined first orientation, and/or the second position of the origin $O_2$ of said left eye reference system with the predetermined second position of the origin $O_2$ in the predetermined second conditions for verifying if said second position of the origin $O_2$ is different from said predetermined second position and/or the second orientation of said left eye reference system with said predetermined second orientation in the predetermined second conditions for verifying if said second orientation is different from said predetermined second orientation;

H) when said first position of the origin $O_1$ of said right eye reference system is different from said predetermined first position of the origin $O_1$ and/or said first orientation of said right eye reference system is different from said predetermined first orientation, reconfiguring said right correction scheme $SC_{DX}$ based on said first position of the origin $O_1$ and/or said first orientation, so that said one or more first digital filters 11 are applied to respective first portions of video frame, different from said predetermined first portions of video frame, and/or when said second position of the origin $O_2$ of said left eye reference system is different from said predetermined second position of the origin $O_2$ and/or said second orientation is different from said predetermined second orientation, reconfiguring said left correction scheme $SC_{SX}$ based on said second position of the origin $O_2$ and/or said second orientation, so that one or more second digital filters 12 are applied to one or more respective second portions of video frame, different from said predetermined second portions of video frame;

I) applying said right correction scheme $SC_{DX}$ to at least one second video frame $FD2_1, FD2_2 \ldots FD2_N$ of said second digital video stream FD2 in such a way that said one or more first digital filter 11 is/are applied to at least one first portion of video frame, so as to obtain a third digital video stream or right digital stream $FD2_{DX}$ intended for the right eye 1, different from said second digital video stream FD2, wherein said right digital stream $FD2_{DX}$ comprises at least one modified second video frame $FD2_1', FD2_2' \ldots FD2_N'$, and/or said left correction scheme $SC_{SX}$ to at least one second video frame $FD2_1, FD2_2 \ldots FD2_N$ of said second digital video stream FD2 in such a way that said one or more second digital filters 12 is/are applied to at least one second portion of video frame, so as to obtain a fourth digital video stream or left digital stream $FD2_{SX}$ intended for the left eye 2, different from said second digital video stream FD2, wherein said left digital stream $FD2_{SX}$ comprises at least one further modified second video frame $FD2_1''$, $FD2_2'' \ldots FD2_N''$;

L) generating a multiview digital video stream MV comprising a first sequence of video frames associated with said second digital video stream FD2 or said right digital video stream $FD2_{DX}$ and a second sequence of video frames associated with said second digital video stream FD2 or said left digital video stream $FD2_{SX}$;

M) displaying said multiview digital video stream MV by means of a stereoscopic video system 7 in such a way that said first sequence of video frames of said multiview digital video stream MV is seen by the right eye 1, and that said second succession of video frames of said multiview digital stream MV is seen by the left eye 2.

With reference to step A), it is specified that a first digital video stream FD1 is acquired, which comprises a succession of first video frames $FD1_1$, $FD1_2 \ldots FD1_N$.

In particular, said first video frames of said first digital stream FD1 can be test video frames configured to individuate the shape, the size and the position of video frame portions in correspondence of which respective visual defects (step B) are perceived and to determine digital filters to eliminate and/or mitigate the perception of said visual defects (step C).

Each of said first video frames can be a respective Amsler grid.

In other words, said first digital video stream is a configuration digital video stream, in the sense that on it shape, size and position of video frame portions are identified, in correspondence of which respective visual defects are perceived and digital filters for eliminating and/or mitigating the perception of said visual defects are determined.

In particular, said first digital video stream FD1 is reproduced from a first video source SV1, which is preferably a computer, and is acquired by a correction device 6, as mentioned above, connected to said first video source.

With reference to step B), it is specified that, with reference to the succession of first video frames, at least one first portion of video frame and/or at least one second portion of video frame is identified, in correspondence with each of them a respective visual defect being perceived by the person, when he/she looks at a display area A, with only the right eye and with only the left eye 2 respectively.

With reference to a portion of video frame, at least one first visual defect may be perceived by a person who looks with the right eye 1. This may be caused by the presence of at least one first retina area which is affected by a first degenerative pathology.

As an alternative or in addition to said at least one first visual defect, a second visual defect can be perceived by a person who looks at the display area A with the left eye 2. This can be caused by the presence of at least one second retina area which is affected by a second degenerative pathology.

Each area of the retina suffering from a degenerative disease such as to cause the perception of a visual defect has a shape, a size and a position. Therefore, visual defects perceived by a person watching a first video frame $FD1_1$, $FD1_2 \ldots FD1_N$ of said first digital video stream FD1 are located in video frame portions corresponding to respective areas of the retina suffering from a degenerative disease.

A degenerative disease of the retina can cause a 'distorted' or 'blurred' vision in correspondence of a portion of video frame, in a more or less accentuated manner.

When the vision is "distorted", visual information relating to said video frame portion is perceived by a person as morphologically altered and/or incomplete.

When the vision is "blurred", visual information relating to that portion of video frame is perceived by a person as obscured and/or with a reduced degree of sharpness.

In both cases, if the retinal degenerative disease does not cause a loss of visual information in said video frame portion, the corrected visual information can be retrieved and the method, subject-matter of the invention, allows to eliminate the perception of the visual defect.

Instead, if the degenerative disease of the retina causes a loss of visual information in said video frame portion, the correct visual information cannot be retrieved and the method of the invention allows to mitigate the perception of visual defect.

In order to determine the shape, the size and the position of said first portion of video frame in correspondence of which a first visual defect is perceived, reference is made to a predetermined first position of the origin $O_1$ and to a predetermined orientation of the of right eye reference system such that the above-mentioned predetermined first conditions are met.

In particular, the eye fixation point P coincides with the center of said display area A, in turn coincident with the origin O of the reference system of the same display area A, and the first axis $x_1$ and the second axis $y_1$ of the first eye reference system are respectively parallel to the first axis x and the second axis y of the display reference system.

Consequently, the third axis $z_1$ of said first eye reference system is aligned to the third axis z of said display reference system.

In order to determine the shape, the size and the position of said second portion of video frame in correspondence of which a second visual defect is perceived, reference is made to a predetermined second position of the origin $O_2$ and at a predetermined second orientation of the left eye reference system such that the above-mentioned predetermined second conditions are met.

In particular, the eye fixation point P coincides with the center of said display area A, in turn coincident with the origin O of the reference system of the same display area A, and the first axis $x_2$ and the second axis $y_2$ of the second eye reference system are respectively parallel to the first axis x and the second axis y of the display reference system.

Consequently, the third axis $z_2$ of said second eye reference system is aligned with the third axis z of the display reference system.

With reference to step C), said one or more first digital filters 11 and/or said one or more second digital filters 12 are configured to modify the value of one or more pixels of one or more of video frame portions, according to a respective predetermined algorithm.

As is known, the value of a pixel is a numeric value that represents the data sampled and quantized by a sensor.

In particular, the value of a pixel can be modified according to the value of the same pixel and/or of a plurality of pixels at a predetermined distance from it or of all of the pixels of said at least one portion of said video frame.

Each first digital filter 11 and each second digital filter 12 is determined based on the visual defect caused by the area of the retina suffering from a degenerative disease.

It is preferable that the number of the first digital filters 11 is at least equal to the number of the first areas of the right eye retina suffering from a degenerative disease and that the number of second digital filters 12 is at least equal to the number of second areas of the left eye retina suffering from a degenerative disease of the retina.

For example, if the right eye 1 has two areas of the retina suffering from a degenerative disease and the left eye 2 has a single area of the retina affected by a disease of the retina, at least two first digital filters 11 are provided to the right eye 1 in order to correct or mitigate the visual defect resulting from a respective area of the retina, and at least one second digital filter 12 is provided for the left eye 2 in order to correct or mitigate the visual defect resulting from said single retina area.

With reference to step D, a respective correction scheme $SC_{DX}$, $SC_{SX}$ is provided for each eye 1,2 and comprises a respective number of digital filters to eliminate and/or mitigate the perception of one or more visual defects in correspondence to respective portions of video frame.

In addition, each of said correction schemes $SC_{DX}$, $SC_{SX}$ has a graphic format so that it is displayed with a respective predetermined image.

The fact that such correction schemes have a respective graphic format allows the respective digital filters to be represented graphically in respective portions of the respective predetermined image, on the basis of the shape, size and position of each of said video frame portions on which a respective filter must be applied.

In other words, each first digital filter 11 belonging to said right correction scheme $SC_{DX}$ is graphically represented in a respective portion of said predetermined first image and each second digital filter 12 belonging to said left correction scheme $SC_{SX}$ is represented graphically in a respective further portion of said predetermined second image.

So, each correction scheme $SC_{DX}$, $SC_{SX}$ may be displayed as an image via any image viewer program able to interpret the graphic format.

With reference to step E), a second digital video stream FD2 comprising a plurality of second video frames $FD2_1$, $FD2_2 \ldots FD2_N$ is provided by a second video source SV2 and acquired by a correction device 6, as mentioned above, connected to said second video source.

Said second source SV2 can be either the first source SV1 and a source different from said first source SV1, such as a computer or a video camera or receiving means for receiving television signals, as mentioned above.

Said second digital video stream FD2 is the digital stream that is modified in order to eliminate and/or mitigate the perception of visual defects caused by the degenerative disease of the retina so that the person suffering from such degenerative disease has a corrected or improved binocular vision of said second digital video stream FD2.

As anticipated, said second digital video stream FD2 is relative to any visual content.

For example, the visual content of said second video source SV2 can be an image or a recorded video (when the second video source is configured to read data stored in a storage device), a television broadcast (when the second video source is configured to receive a digital TV signal), a live video (when the second video source is configured to retrieve a video), a video output of a computer (when the second video source is configured to read data from a video card of a computer).

Said second digital video stream FD2 is acquired by said correction device 6, connected to said second video source SV2.

With reference to step F), it is specified that at least two parameters are calculated for each eye with respect to the display reference system:

a first position of the origin $O_1$ and a first orientation of the right eye reference system, and
a second position of the origin $O_2$ and a second orientation of the left eye reference system.

Such positions and said orientations are calculated by means of a tracking system to track the eye fixation point, as mentioned above.

For example, said tracking system can be a known type of optical tracking system and configured to calculate said parameters by means of video-oculography techniques.

With reference to step G), the method provides for a comparison between the first position of the origin $O_1$ of the right eye reference system, calculated by the tracking system, and the predetermined first position of the origin $O_1$ of the same right eye reference system, and between the first orientation of the right eye reference system, calculated by the tracking system, and the predetermined first orientation of the same right eye reference system, and/or between the second position of the origin $O_2$ of the left eye reference system, calculated by the tracking system, and the predetermined second position of the origin $O_2$ of the same left eye reference system, and between the second orientation of the left eye reference system, calculated using the tracking system, and the predetermined second orientation of same left eye reference system.

With reference to step H), it is specified that:

the right correction scheme $SC_{DX}$ is reconfigured when the first origin position $O_1$ of the right eye reference system is different from the predetermined first position of the same right eye reference system and/or the first orientation of the right eye reference system is different from the predetermined first orientation of the same right eye reference system, and the left correction scheme $SC_{SX}$ is reconfigured when the second origin position $O_2$ of the left eye reference system is different from the predetermined second position of the same left eye reference system and/or the second orientation of the left eye reference system is different from the predetermined second orientation of the same left eye reference system.

In this way, the first digital filters 11 of the right correction scheme $SC_{DX}$ and the second digital filters 12 of the left correction scheme $SC_{SX}$ are applied to respective portions of video frame, different from the above predetermined portions of video frame.

It is necessary that each correction scheme is reconfigured to follow the movement of a respective eye, so that the digital filters of each correction scheme are always applied to video frame portions in correspondence of which a person perceives a visual defect, due to the fact that each eye has one or more retinal areas suffering from a degenerative disease.

Reconfiguring a correction scheme means to perform a digital processing of the predetermined image associated with said correction scheme as a function of the origin position of the eye reference system and/or orientation of the eye reference system.

The processing of the predetermined image associated with the correction scheme can be carried out with different techniques and algorithms of known type.

For example, said processing can be described by a geometrical method.

Before going into the detail of the geometric procedure, to the right correction scheme $SC_{DX}$ a first three-dimensional Cartesian reference system is associated, which is identified by the triad of axes $x_3$, $y_3$, $z_3$, integral with said right correction scheme, and to the left correction scheme $SC_{SX}$ a second three-dimensional Cartesian reference system is associated, which is identified by the triad of axes $x_4$, $y_4$, $z_4$, integral with said left correction scheme.

Each three-dimensional Cartesian reference system has a respective origin $O_3$, $O_4$.

Such processing may comprise the following substeps:

i) moving the right correction scheme $SC_{DX}$ and/or the left correction scheme $SC_{SX}$ integrally to the movement of the respective eye, so that the first Cartesian three-dimensional reference system and/or the second three-dimensional Cartesian reference system follows/follow the movement of the respective eye in such a way as to remain integral respectively to the first visual axis V1 and the second visual axis V2, and that the first axis $x_3$, $x_4$ and the second axis $y_3$, $y_4$ of a respective Cartesian three-dimensional reference system, respectively, are parallel to the first axis $x_1$, $x_2$ and the second axis $y_1$, $y_2$ of the respective eye reference system. Consequently, the third axis $z_3$, $z_4$ of the respective three-dimensional Cartesian reference system is aligned with the third axis $z_1$, $z_2$ of the respective eye reference system along the respective visual axis V1, V2;

ii) projecting said right correction scheme $SC_{DX}$ on the display plane according to the direction of the first visual axis V1, and/or said left correction scheme $SC_{SX}$ on the display plane according to the direction of the second visual axis V2;

iii) selecting the plurality of points in the display plane included in the display area A in order to obtain the respective reconfigured correction scheme according to the origin position of the respective eye reference system and/or the orientation of said eye reference system.

In the example that is described, a first group of geometric transformations is applied to the right correction scheme $SC_{DX}$ to reconfigure said right correction scheme and/or a second group of geometric transformations is applied to the left correction scheme $SC_{SX}$ to reconfigure said left correction scheme.

Geometric transformations allow to adjust the position and/or orientation of the respective correction scheme to the variation of the origin position of the respective eye reference system and/or orientation of said eye reference system, with respect to the predetermined conditions mentioned above, under which shape, size and position of one or more first portions of video frame and/or one or more second portions of video frame are identified, in correspondence of which a respective visual defect is perceived by a person.

With reference to the right correction scheme $SC_{DX}$, when the predetermined first conditions are no longer satisfied, said first group of geometric transformations may include the following geometric transformations:

at least one shift of the right correction scheme so that the origin $O_3$ of the three-dimensional Cartesian reference system, associated and integral with said right correction scheme $SC_{DX}$, be in any point in space which is different from the origin O of said display reference system, where said point can be outside the display plane as not belonging to it, and/or at least one rotation of said right correction scheme or said shifted right correction scheme so that the first axis $x_3$ and the second axis $y_3$ of the three-dimensional Cartesian reference system, associated and integral with said right correction scheme $SC_{DX}$, are parallel respectively to first axis $x_1$ and the second axis $y_1$ of the right eye reference system.

In addition, when said first group of geometric transformations places said right correction scheme $SC_{DX}$ on a plane different from the display plane (i.e. the plane in which the display area is), said first group of geometric transformations includes a projection of said shifted right correction scheme or of said rotated right correction scheme or said rotated and translated right correction scheme onto said display plane according to the direction of said first visual axis.

Because of said first group of geometric transformations, a first part of said right correction scheme $SC_{DX}$ comprising a first plurality of points may fall within the display area and a second part of said right correction scheme $SC_{DX}$ comprising a second plurality of points may fall outside the display area.

With reference to the left correction scheme $SC_{SX}$, when the predetermined second conditions are no longer fulfilled, said second group of geometric transformations may include the following geometric transformations:

at least one translation of the left correction scheme so that the origin $O_4$ of the second three-dimensional Cartesian reference system, associated and integral with said left correction scheme, be in any point in space, different from the origin O of said reference system display, wherein said point may be a point external to the display plane as not belonging to it, and/or at least one rotation of said left correction scheme or said shifted left correction scheme so that the first axis $x_4$ and the second axis $y_4$ of the second Cartesian reference system, associated and integral with said left correction scheme, are respectively parallel to the first axis $x_2$ and the second axis $y_2$ of the left eye reference system.

In addition, when said second group of geometric transformations places said left correction scheme $SC_{SX}$ on a plane different from the display plane (i.e. the plane to which the display area belongs), said second group of geometric transformations comprises a projection of said shifted left correction scheme or said rotated left correction scheme or said rotated and shifted left correction scheme onto said display plane according to the direction of said second visual axis.

Because of said second group of geometric transformations, a first part of said left correction scheme $SC_{SX}$ comprising a third plurality of points may fall within the display area and a second part of said left correction scheme $SC_{SX}$ comprising a fourth plurality of points may fall outside the display area.

With reference to phase I), it is specified that from said second digital video stream FD2 a third digital video stream or the right digital stream $FD2_{DX}$ and/or fourth digital video stream or left digital stream $FD2_{SX}$ can be generated, by the application by said correction device 6 of a respective correction scheme $SC_{DX}$, $SC_{SX}$ to at least one second video frame $FD2_1$, $FD2_2$ . . . $FD2_N$ of said second digital video stream FD2.

In the case in which the right eye 1 has no retinal area suffering from a degenerative pathology, the right digital stream $FD2_{DX}$ coincides with the digital video stream FD2 and in the case in which the left eye 2 does not have any area of the retina affected from a degenerative disease, the left digital stream $FD2_{SX}$ coincides with the digital video stream FD2.

Advantageously, said right digital flow $FD2_{DX}$ and said left digital stream $FD2_{SX}$ are intended for the right eye 1 and left eye 2, respectively, in such a way that the perceived visual defects resulting from one or more first retina areas of the right eye 1, suffering from a degenerative disease, and/or the perceived visual defects resulting from one or more second retina areas of the left eye 2, suffering from a further degenerative disease, can be eliminated and/or attenuated.

A further advantage is given by the fact that the perceived visual defects due to one or more first retina areas of the right eye, suffering from a degenerative disease, can be eliminated and/or attenuated independently by the perceived visual defects due to one or more second retina areas of the left eye, suffering from a degenerative disease.

With reference to the steps L) and M), it is specified that a multiview digital video stream MV is generated that comprises:
- a first succession of video frames associated with the second digital video stream FD2 (in case no right correction scheme $SC_{DX}$ is applied to a second video frame $FD2_1$, $FD2_2$ . . . $FD2_N$ of said second digital video stream FD2) or to said right digital video stream $FD2_{DX}$ (in case the right correction scheme $SC_{DX}$ is applied to at least one second video frame $FD2_1$, $FD2_2$ . . . $FD2_N$ of said second digital video stream FD2), and
- a second succession of video frames associated with the second digital video stream FD2 (in case no left correction scheme $SC_{SX}$ is applied to a second video frame $FD2_1$, $FD2_2$ . . . $FD2_N$ of said second digital video stream FD2) or to said left digital video stream $FD2_{SX}$ (in case the left correction scheme $SC_{SX}$ is applied to at least one second video frame $FD2_1$, $FD2_2$ . . . $FD2_N$ of said second digital video stream FD2).

In particular, said multiview digital video stream MV is generated by said correction device 6 that is configured to perform a known type of video encoding process compatible with the stereoscopic video system 7.

In this way, said multiview digital video stream MV is encoded in such a way as to be compatible with the stereoscopic video system 7, connected to said correction device 6.

Said multiview digital video stream MV is transmitted by said correction device 6 to said stereoscopic video system 7 and, thanks to the stereoscopic video system, said multiview digital video stream MV is displayed on the display area in such a way that the first sequence of video frames is seen by the right eye 1 and the second sequence of video frames is seen by the left eye 2.

In other words, said stereoscopic video system 7 is only a means by which it is possible to convey a respective succession of video frames to a respective eye.

The same is true if the video system 7 is autostereoscopic.

Advantageously, each eye sees a respective image changed according to the respective visual defects, so that a person who looks with both eyes perceives an image in which the visual defects, perceived because of retinal areas suffering from a degenerative disease, are eliminated and/or attenuated.

In an alternative, although not shown in the figures, said video system 7 may be an autostereoscopic video system, without thereby departing from the scope of the invention.

When the video system is autostereoscopic, the person must occupy a predetermined position with respect to the display area of said autostereoscopic video system, in terms of distance and person's face angle with respect to said display area.

In particular, the distance and the angle with which the said person looks at said display area must be such that said first sequence of video frames of said multiview digital video stream MV is seen by the right eye 1, and that said second succession of video frames of said multiview digital stream MV is seen by the left eye 2.

In addition, the correction device 6 is configured to perform a video encoding compatible with said autostereoscopic video system.

With reference to the steps of the above described method, if the person moves further the right eye 1 and/or the left eye 2, both the eyes and/or the head, said method may further comprise the following steps:

F') calculating
for the right eye 1, a further first position of the origin $O_1$ and a further first orientation of said right eye reference system with respect to said display reference system, and/or
for the left eye 2, a further second position of the origin $O_2$ and a further second orientation of said left eye reference system with respect to said display reference system;

G1) comparing
said further first position of the origin $O_1$ of said right eye reference system with said predetermined first position of the origin $O_1$ in the predetermined first conditions to verify if said further first position of the origin $O_1$ of said right eye reference system is different from said predetermined first position and/or said further first orientation of said right eye reference system with said predetermined first orientation in the predetermined first conditions to verify if said further first orientation is different from said predetermined first orientation, and/or
said further second position of the origin $O_2$ of said left eye reference system with said predetermined second position of the origin $O_2$ in the predetermined second conditions to verify if said further position of the origin $O_2$ is different from said predetermined second position and/or said further second orientation of said left eye reference system with said predetermined second orientation in the predetermined second conditions to verify if said further second orientation is different from said predetermined second orientation;

G2) for the right eye, comparing:
said further first position of the origin $O_1$ of said right eye reference system with said first position to verify if said further first position of the origin $O_1$ is different from said first position of the origin $O_1$, when said further first position of the origin $O_1$ of said right eye reference system is different from the predetermined first position of the origin $O_1$ in the predetermined first conditions, and/or
said further first orientation of said right eye reference system with said first orientation to verify if said further first orientation is different from said first orientation, when said further first orientation of said right eye reference system is different from the predetermined first orientation in the predetermined first conditions,
and/or
for the left eye, comparing
said further second position of the origin $O_2$ of said left eye reference system with said second position of the origin to verify if said further second position of the origin $O_2$ is different from said second position of the origin $O_2$, when said further second position of the origin $O_2$ of said left eye reference system is different from said predetermined second position of the origin $O_2$ in the predetermined second conditions, and/or
said further second orientation of said left eye reference system with said second orientation to verify if said further second orientation is different from said second orientation when said further second orientation of said left eye reference system is different from said predetermined second orientation in the predetermined first conditions;

H') reconfiguring said right correction scheme $SC_{DX}$ based on said further first position of the origin $O_1$ as calculated, when said further first position of the origin $O_1$ of said right eye reference system is different from said first position of the origin $O_1$, and/or, on the basis of said further first orientation as calculated, when said further first orientation is different from said first orientation, and/or reconfiguring said left correction scheme $SC_{SX}$ based on said further second position of the origin $O_2$ as calculated, when said further second position of the origin $O_2$ of said left eye reference system is different from said second position of the origin $O_2$, and/or on the basis of said further second orientation as calculated, when said further second orientation is different from said second orientation.

Figure 3A:
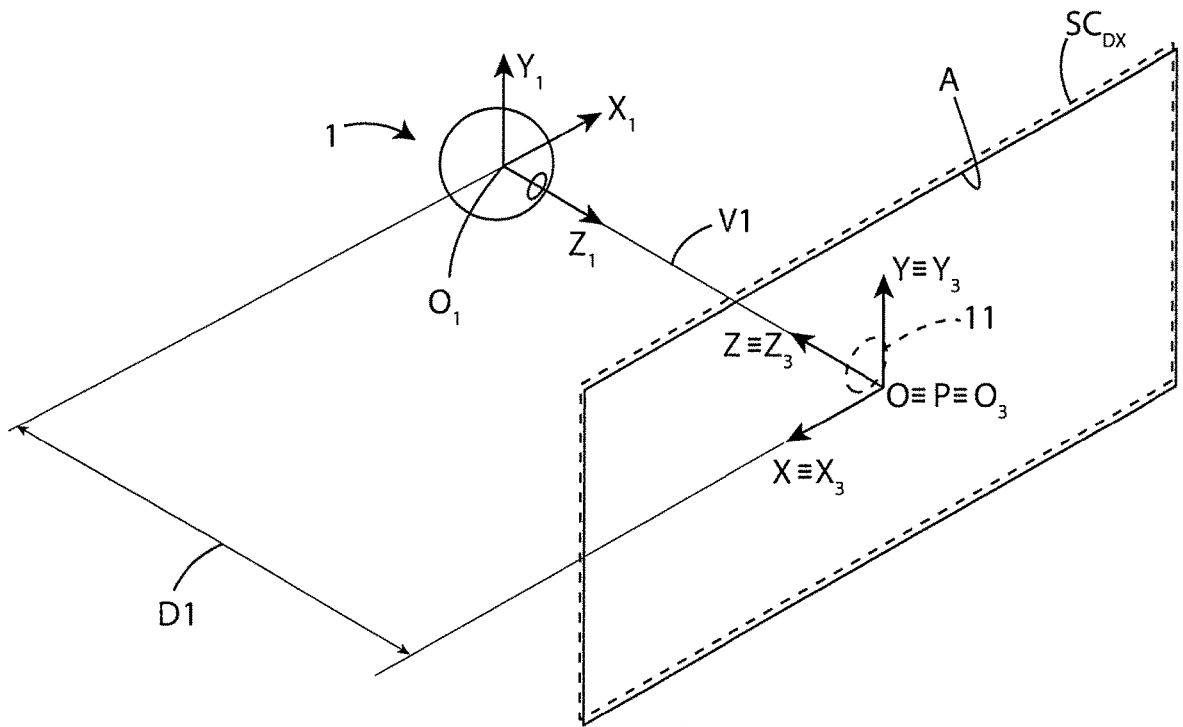

With reference to FIG. 3A onwards, some steps of the method are shown, once the right correction scheme $SC_{DX}$ and the left correction scheme $SC_{SX}$ have been configured respectively for the right eye 1 and for the left eye 2, when the predetermined conditions mentioned above are verified.

In the example that is described, each eye has respectively a first retinal area and a second retinal area affected by a respective degenerative pathology.

Consequently, each correction scheme $SC_{DX}$, $SC_{SX}$ respectively comprises a first digital filter 11 and a second digital filter 12.

Depending on the perceived visual defect due to degenerative disease, it is possible to provide an appropriate digital filter.

If the degenerative disease is such that a portion of video frame in correspondence of a retina area is perceived as distorted in a first direction without there being a loss of information, the digital filter is a digital filter with distorting effect to distort the first portion of video frame in a second direction, opposite to said first direction, to compensate for the visual defect perceived by the person. In this way, with reference to said portion of video frame, the binocular vision is corrected.

For example, if the degenerative disease of the retina is such that a person has a distorted visual perception to the left or to the right of a portion of video frame, the digital filter is configured to distort to an extent equal to the same portion of video frame, respectively, towards the right or the left to compensate for the visual defect perceived by the person, so that the portion of the image in correspondence with said portion of video frame is seen correctly or substantially correctly.

If the pathology is such as to cause, with reference to a portion of video frame in correspondence of a retina area, an altered visual perception that cannot be corrected, for example in the case of a distortion with loss of information, the digital filter can be a digital filter with blur effect to blur said video frame portion.

Where a first eye is healthy (i.e. not suffering from degenerative diseases) or not suffering from degenerative disease in a retina area corresponding to the one in the second eye that is suffering from degenerative pathology, binocular vision of the image portion in correspondence of said portion of video frame produces a faded visual perception. This is due to the application of the digital filter with blur effect to eliminate the perception of visual defects of the second eye. How much this perception is faded depends on the merging process carried out by the brain that takes into consideration, with different weights, the contributions of the first eye and the second eye, which relate to the same image portion perceived corrected and blurred respectively.

With the method of the invention, it is possible to reduce the weight of the altered informative contribution supplied by the second eye, improving the perception of the information content of said video frame portion.

In particular, as can be seen from FIG. 3A, the right eye 1 is at a predetermined first distance D1 from said display area A, and the first axis $x_1$ and the second axis $y_1$ of the first eye reference system are parallel respectively to the first axis x and the second axis y of the display reference system, and the third axis $z_1$ of the first eye reference system is aligned to the third axis z of the display reference system.

In particular, the third axis $z_1$ of the first eye reference system and the third axis z of the display reference system are aligned along the first visual axis V1, and then the eye fixation point P coincides with the origin O of the display reference system.

In addition, the right correction scheme $SC_{DX}$ is displayed with a predetermined first image, which is the graphic representation of said right correction scheme, and to the first digital filters 11 of said right correction scheme $SC_{DX}$ is associated with a respective portion of said predetermined first image.

In the example that is being described, the first digital filter 11 is positioned in the vicinity of the center of the display area A with respect to whom looks at said display area.

In FIG. 3A, the right correction scheme $SC_{DX}$ is represented by a rectangle with a dashed line and the display area A is represented by a rectangle with continuous line.

Said right correction scheme $SC_{DX}$ is superimposed to the display area A to show the correspondence between each point of the right correction scheme $SC_{DX}$ and a respective point of the display area A on which each video frame is displayed.

In FIG. 3A, the predetermined distance between the right eye 1 and the display area A are also shown, and the position and the orientation of the right eye reference system, as identified by the set of three axes $x_1$, $y_1$, $z_1$, with respect to the display reference system, as identified by the set of three axes x, y, z.

The eye fixation point P coincides with the center of the display area A.

In other words, FIG. 3A shows the situation in which the predetermined first conditions are met.

In such a situation, as can be seen from FIG. 3A, the three-dimensional Cartesian reference system as identified by the triad of axes $x_3$, $y_3$, $z_3$, integral to and associated with the right correction scheme $SC_{DX}$, coincides with the display reference system.

Figure 3B:
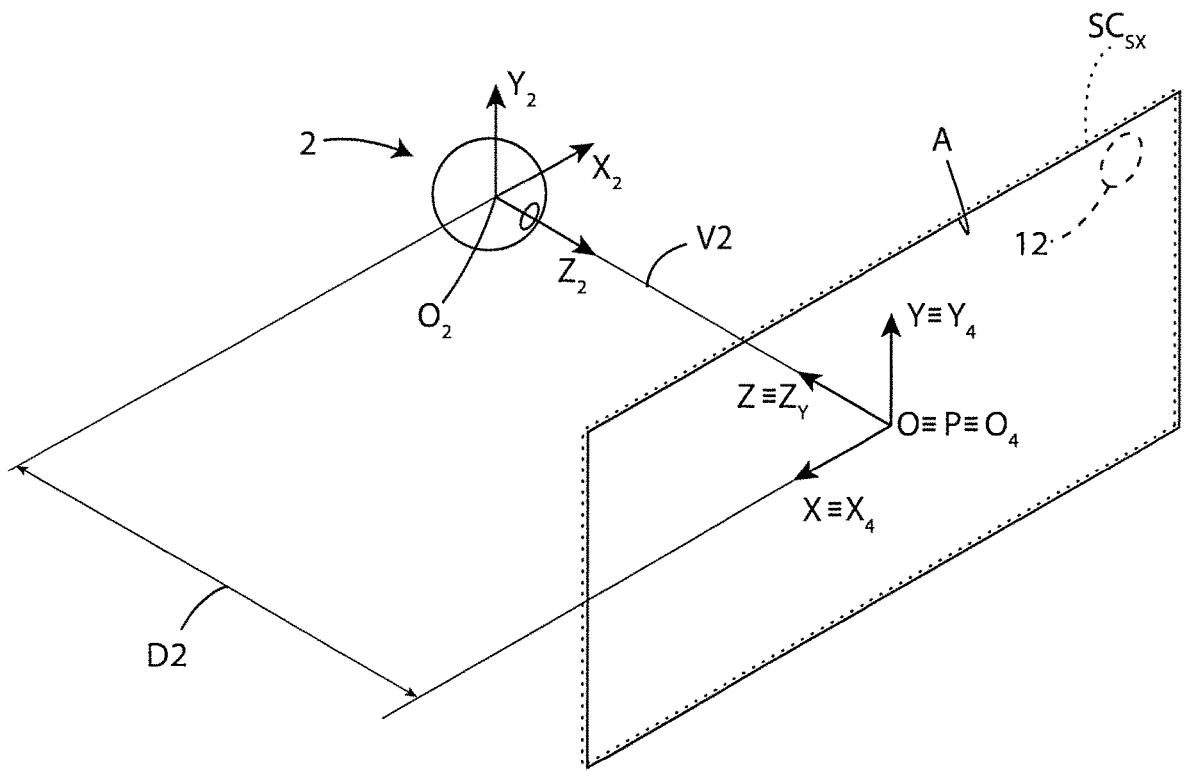

As can be seen from FIG. 3B, the left eye 2 is at a predetermined second distance D2 from said display area A, and the first axis $x_2$ and the second axis $y_2$ of the second eye reference system are parallel respectively to the first axis x and the second axis y of the display reference system, and the third axis $z_2$ of the second eye reference system is aligned to the third axis z of the display reference system.

In particular, the third axis $z_2$ of the second eye reference system and the third axis z of the display reference system are aligned along the second visual axis V2, and then the eye fixation point P coincides with the origin O of the display reference system.

In addition, the left correction scheme $SC_{SX}$ is displayed with a predetermined second image which is the graphic representation of said left correction scheme and to the second digital filters 12 of said left correction scheme $SC_{SX}$ is associated with a respective predetermined portion of said second image.

In the example that is being described, the second digital filter 12 is positioned in the vicinity of the angle formed by two consecutive sides of the display area A, in the upper left with respect to whom looks at said display area.

In FIG. 3B, similarly to FIG. 3A, the left correction scheme $SC_{SX}$ is represented by a rectangle with a dashed line and the display area A is represented by a rectangle with continuous line.

Said left correction scheme $SC_{SX}$ is superimposed to the display area A to show the correspondence between each point of the left correction scheme $SC_{SX}$ and a respective point of the display on which is displayed each video frame.

In FIG. 3B, the predetermined distance between the left eye 2 and the display area A are also shown, as well as the position and the orientation of the left eye reference system, as identified by the set of three axes $x_2$, $y_2$, $z_2$, with respect to the display reference system, as identified by the set of three axes x, y, z.

The eye fixation point P coincides with the center of the display area A.

In other words, FIG. 3B shows the situation in which the predetermined second conditions are met.

In such a situation, as can be seen from FIG. 3B, the three-dimensional Cartesian reference system identified by the triad of axes $x_4$, $y_4$, $z_4$, integral to and associated with the right correction scheme $SC_{SX}$, coincides with the display reference system.

In the example that is described, said right correction scheme $SC_{DX}$ and said left correction scheme $SC_{SX}$ are associated with predetermined images that have shape and size equal to those of the display area.

Figure 4:
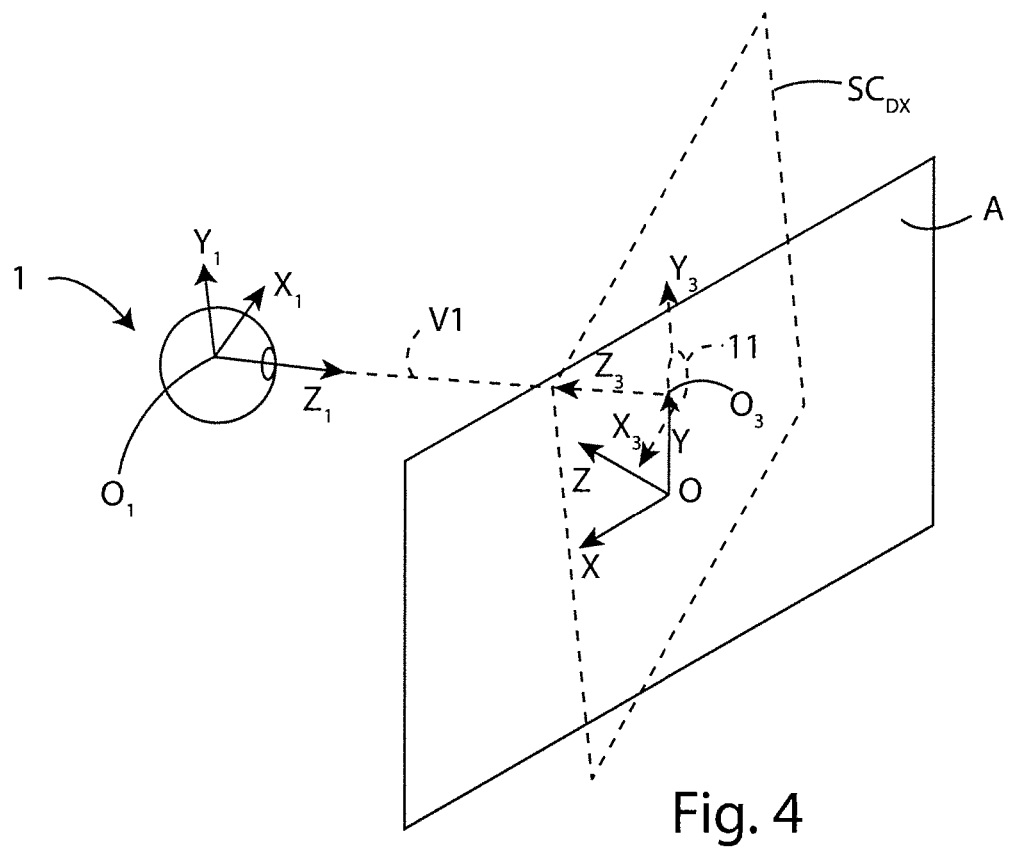
Figure 5:
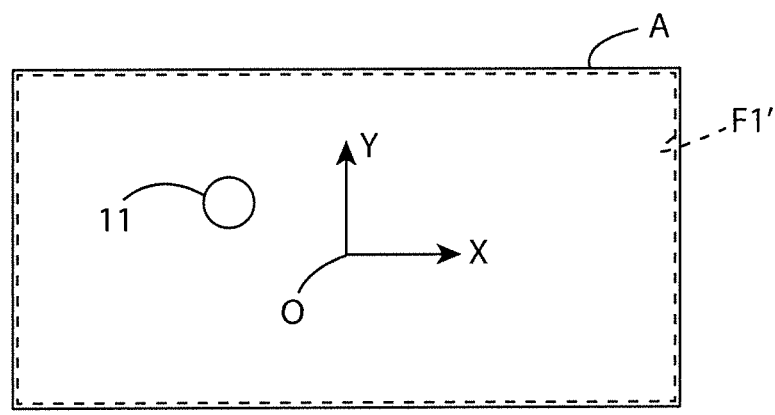
Figure 6:
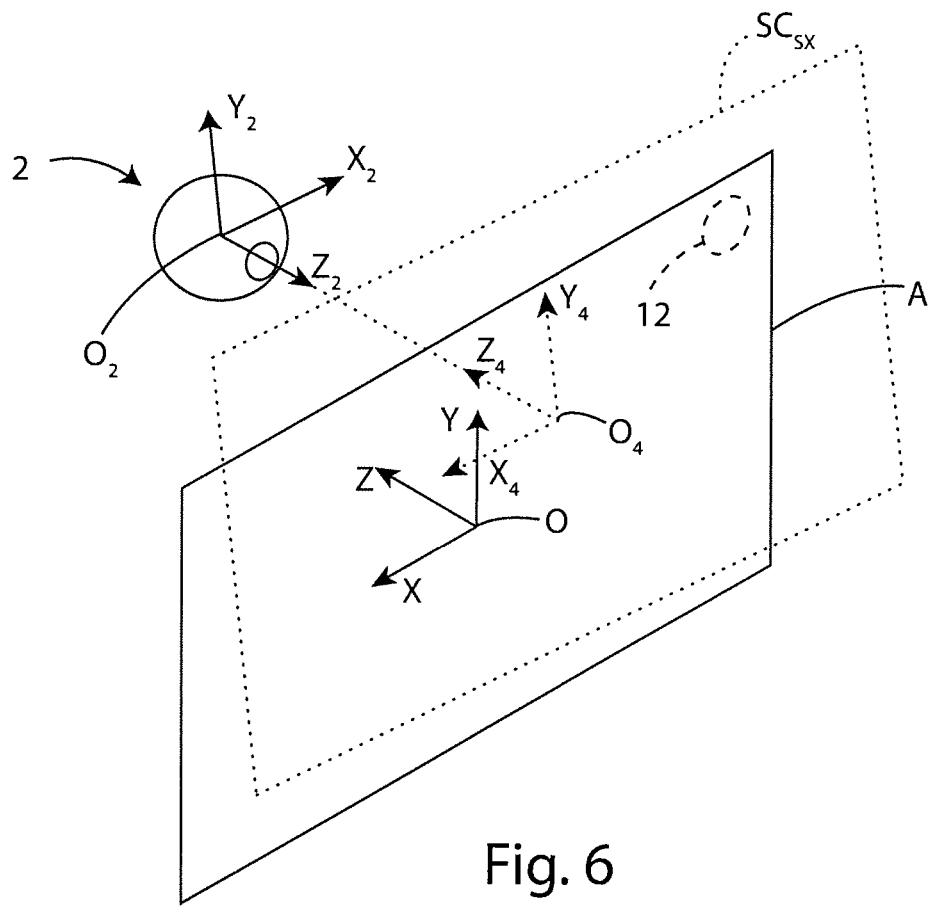
Figure 7:
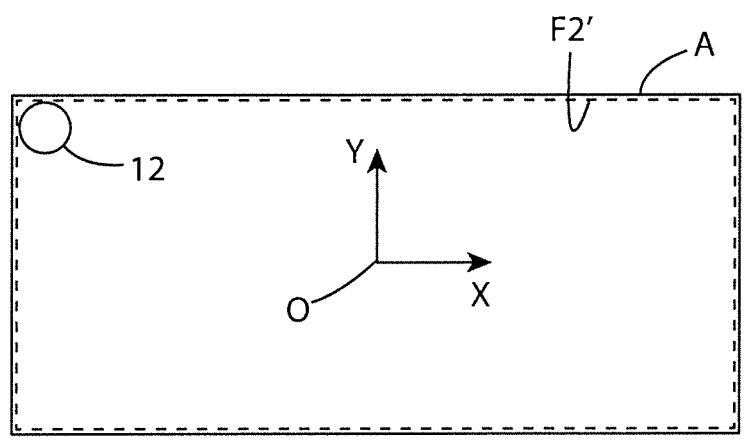
FIG. 7 shows the situation in which said second rototraslated correction scheme has been projected on a display plane passing through the display area according to the direction of the second visual axis and a second image is shown including the points of the display plane included in the display area.

With reference to FIGS. 4 and 5, as well as to FIGS. 6 and 7, the situation is shown in which the eye fixation point P has changed position on the display area A with respect to the original position where it coincided with the origin O of of display reference system.

This can be achieved with a movement of the eyes and/or head of a person.

With particular reference to FIG. 4, the right eye 1 and the first correction scheme are shown, wherein the first correction scheme has been translated and rotated with respect to the display area A in such a way that takes into account information relating to the eye fixation point position and to orientation of the first eye reference system with respect to the display reference system.

Accordingly, the first Cartesian system integral to and associated with the predetermined first image of the right correction scheme $SC_{DX}$ no longer coincides with the display reference system.

To obtain the first image F1' displayed on said display area A shown in FIG. 5, the translated and rotated correction scheme $SC_{DX}$ is projected onto the display plane according to the direction of the first V1 visual axis.

Due to the translation, rotation and projection of the right correction scheme $SC_{DX}$ on the display plane, a first part of the predetermined first image of said first correction scheme comprising at least a first plurality of points falls within the display area A and a second part of said predetermined first image comprising a second plurality of points falls outside the display area.

In FIG. 5, the display area A and the first image F1' displayed on said display area A are shown.

Said first image F1' comprises the points of the display plane that fall within the display area.

As it can be seen from FIG. 5, the first digital filter 11 has changed shape, size and is located in a new position, different from the original one (in the vicinity of the origin O of the display reference system). In fact, the first digital filter 11 is in a decentralized position with respect to the center of the display area A.

With particular reference to FIG. 6, the left eye 2 and the left correction scheme $SC_{SX}$ is shown, which has been translated and rotated with respect to the display area A in such a way that takes into account information relating to the position of the eye fixation point P and orientation of the second eye reference system with respect to the display reference system.

Consequently, the second Cartesian system integral to and associated with the predetermined second image of the left correction scheme $SC_{SX}$ no longer coincides with the display reference system.

To obtain the second image F2' displayed on said display area A shown in FIG. 7, the translated and rotated left correction scheme $SC_{SX}$ is projected onto the display plane passing through the display area in accordance with the direction of the second visual axis V2.

Due to the translation, rotation and projection of the left correction scheme $SC_{SX}$ on the display plane, a first part of said predetermined second image comprising at least a third plurality of points falls within the display area A and a second part of said predetermined second image comprising a fourth plurality of points falls outside the display area.

In FIG. 7, the display area A and the second image F2' displayed on said display area are shown.

Said second image F2' includes the points of the display plane that fall within the display area.

As can be seen from FIG. 7, the second digital filter 12 has changed shape, size and is located in a position different from the original one. In fact, the second digital filter is in a position such that two portions of said second digital filter 12 are substantially in contact with a respective side of the display area A.

In the example of application described above, each predetermined image of the respective correction scheme is subject to a respective group of geometric transformations comprising not only a translation and a rotation, but also a projection onto the display plane according to the respective visual axis.

In FIG. 8, an image corresponding to a video frame as provided by a video source and displayed on the display area A is shown.

As can be seen from FIG. 8, said image is an array of integers, where said numbers matrix has four rows and nine columns.

If both eyes of a person had not one or more retinal areas suffering from a degenerative disease, the image provided by the video source would be seen and perceived by the person as shown in FIG. 8.

Figure 9A:
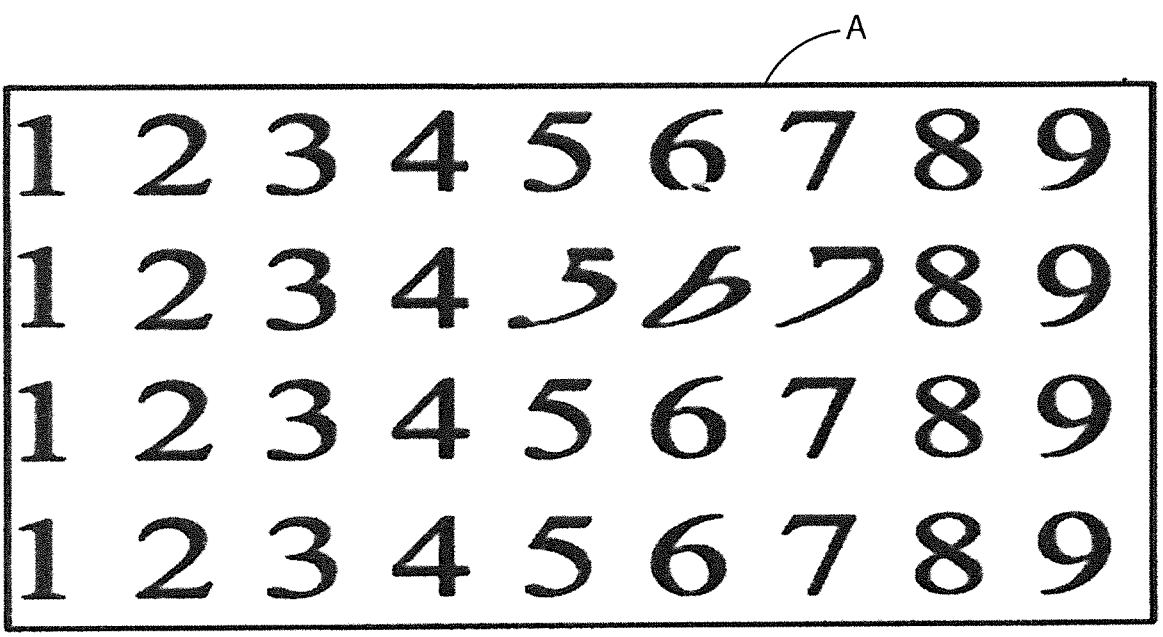
FIGS. 9A, 9B and 9C show the same frame as in FIG. 8 as it would be perceived by a person suffering from a degenerative retinal disease that looks at the center of said image, respectively with the only right eye, with only the left eye and both eyes.
Figure 9B:
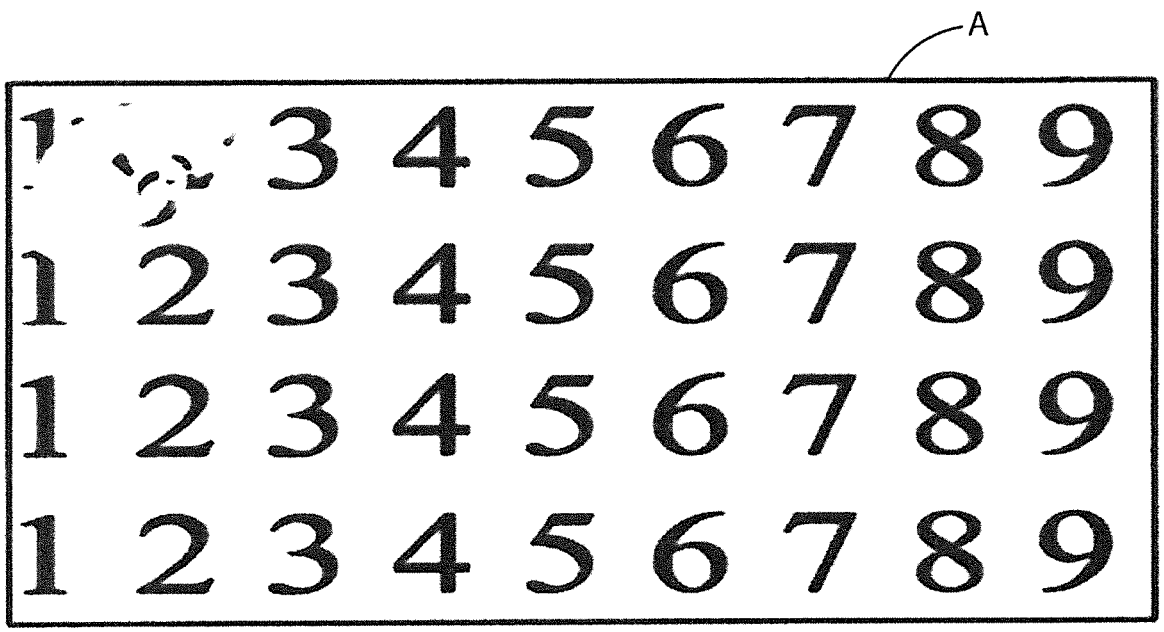
Figure 9C:
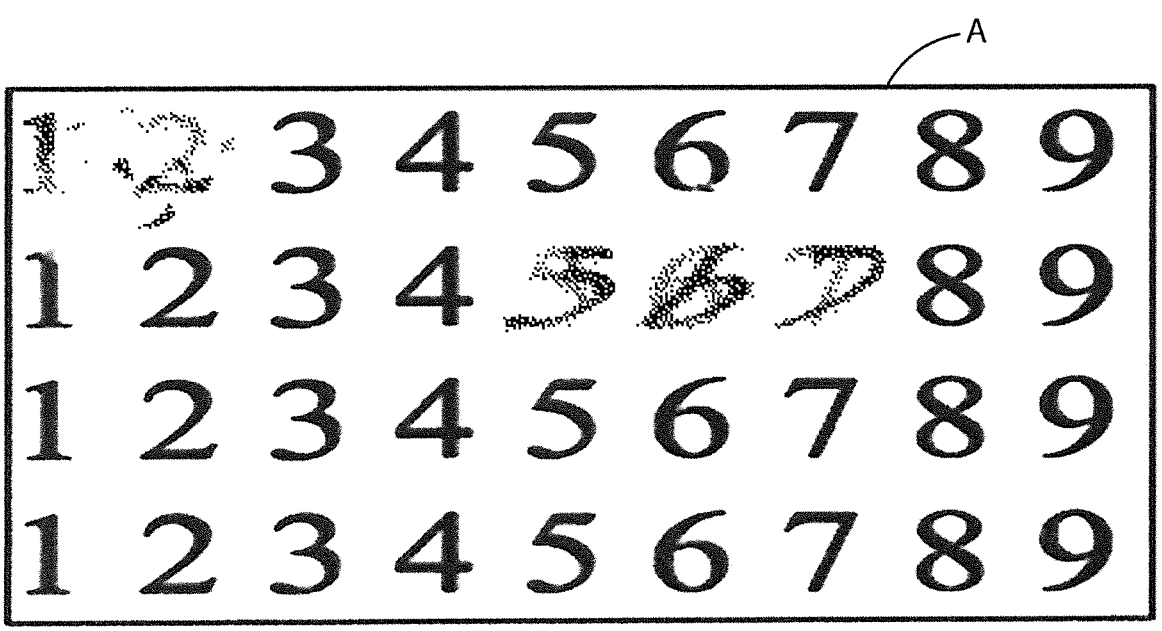

In FIGS. 9A, 9B, 9C the same image of FIG. 8 is shown as it is perceived by a person who looks only with the right eye, only with the left eye and with both eyes, respectively.

That person has the retina of each eye suffering from a respective degenerative disease that causes the perception of a respective visual disturbance, in correspondence with a respective portion of said image.

As can be seen from FIGS. 9A and 9B, a right eye retina area is suffering from a degenerative disease such that the person perceives a first image portion distorted to the right, i.e. deformed but without loss of information, while a retina area of the left eye is suffering from a degenerative disease such that the person perceives a second portion of the image altered so as to have a loss of visual information in correspondence with said second portion of the image (irreversible distortion).

When no correction scheme is applied, the binocular vision of the same image (FIG. 9C) combines the two altered visual perceptions caused by degenerative diseases affecting the respective areas of the retina of the single eyes. This is due to the merging process, carried out by the brain, of the signals which from the two eyes reach the brain itself.

In general, without going into detail of the merging process by the brain of the signals from the two eyes, and neglecting any situations that may cause a failure of said merging process, causing dynamic effects (such as image flicker, doubling of image or alternation of parts of the image) the binocular vision of the image shown in FIG. 8 by the person suffering degenerative diseases of the retina described above could cause a perception of the image similar to that shown in FIG. 9C, which is the result of the merger performed by the brain, with respective weights of the signals arising from the right monocular vision and left monocular vision.

Figure 10A:
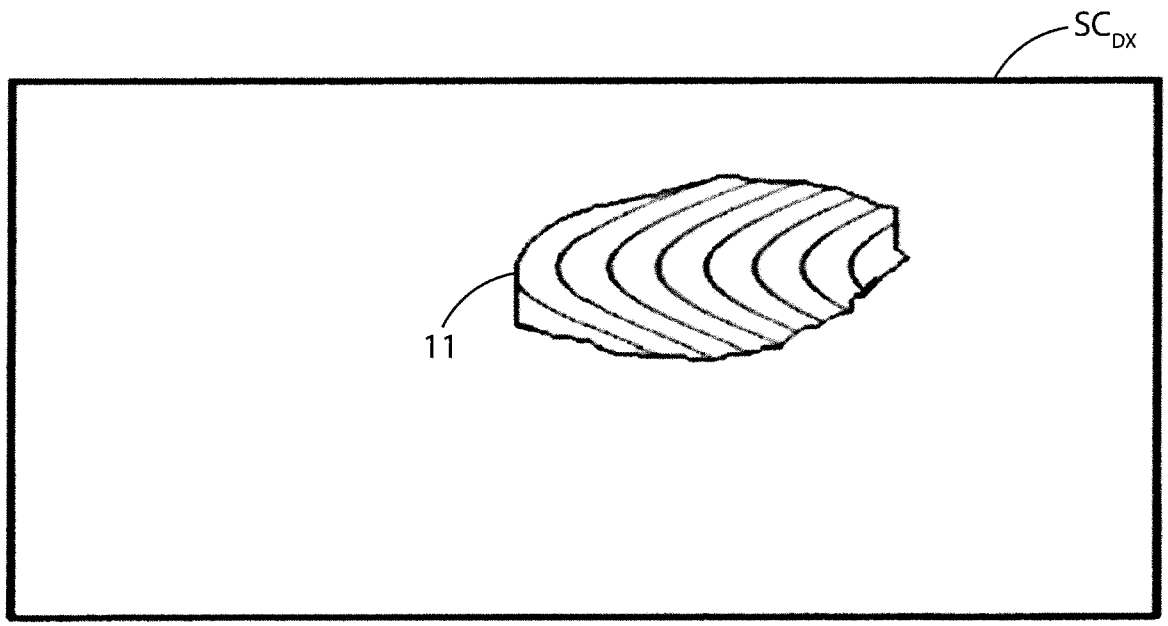
FIGS. 10A and 10B show respectively the first correction scheme and the second correction scheme, each comprising a respective digital filter.
Figure 10B:
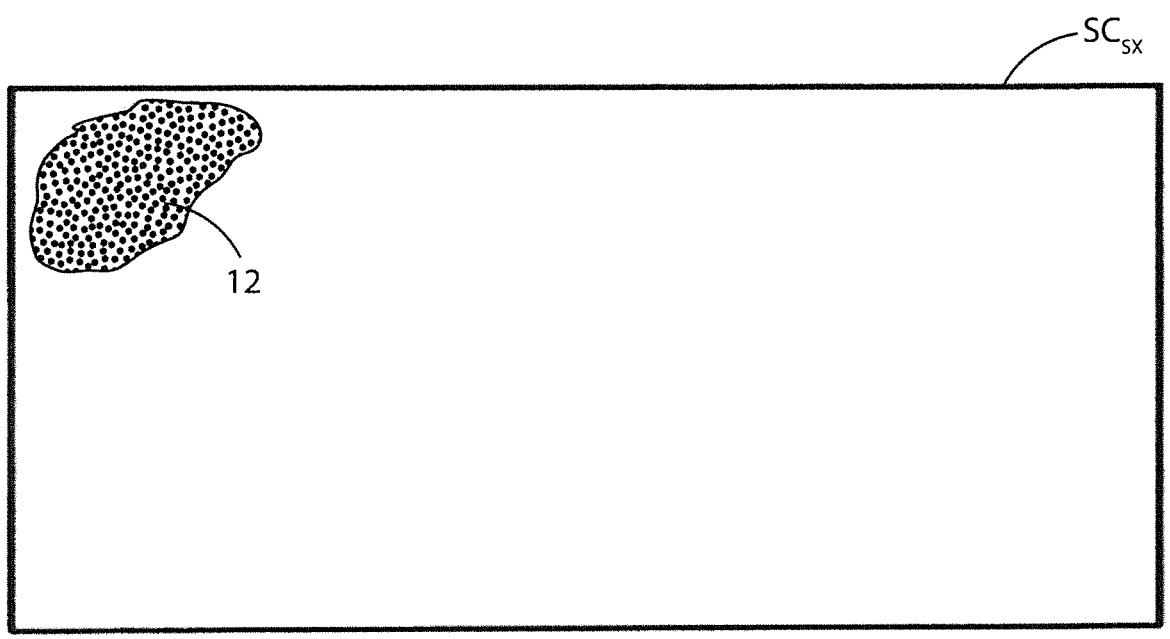

In FIGS. 10A and 10B, the right correction scheme $SC_{DX}$ and the left correction scheme $SC_{SX}$ are respectively shown, each of which respectively comprises a first digital filter 11 and a second digital filter 12.

The first digital filter 11 is a digital filter with distorting effect to distort to the left a portion of the image displayed in the video framework.

The second digital filter 12 is a digital filter with blurring effect to blur a portion of the image shown in the video frame that is perceived to be altered with a loss of information.

FIGS. 11A and 11B represent respectively the images corresponding to the video frame of FIG. 8, as perceived by a person whose retinas are not suffering from degenerative diseases, after the application of the first digital filter 11 and the second digital filter 12.

FIGS. 12A and 12B represent respectively the images corresponding to the video frame of FIG. 8, as perceived by a person whose retinas are suffering from retinal degenerative diseases, when he/she looks with only the right eye 1 after the right correction scheme $SC_{DX}$ has been applied to the image, and when he/she looks with only the left eye 2, after the left correction scheme $SC_{SX}$ has been applied to the same image.

FIG. 12C shows the image corresponding to the video frame of FIG. 8 as perceived by the person suffering from retinal degenerative diseases when looking with both eyes.

In other words, the displayed image is the representation of the image perceived by said person as a result of the merger of the right eye 1 and the left eye 2 contributions.

The fact that the binocular vision of an image is always the result of an elaboration made by the brain of the signals that both eyes send to the brain is to be considered.

As it can be seen from FIG. 12C, the perception of the first portion of the image (initially perceived as portion distorted to the right) has been corrected by the application of the right correction scheme $SC_{DX}$ and the perception of the second portion of the image (initially perceived as a portion whose visual information is altered with loss of information) has been made such that said second portion of the image is faded by the application of the left correction scheme $SC_{SX}$.

Advantageously, by the method and the system, subject-matter of the invention, one or more digital images of a digital video stream reproduced on a display area of a display device of an autosteroscopic or stereoscopic system are modified through respective correction schemes for the right eye and for the left eye in order to compensate for visual defects perceived by each eye of the subject suffering from a degenerative disease of the retina.

The application of said respective correction schemes on said digital video stream allows to generate two further digital video streams (each of which is destined to a respective eye), so that the perception of visual defects in a subject suffering from a degenerative disease of the retina is deleted and/or attenuated and its binocular vision is improved.

The present invention has been described for illustrative but not limitative purposes, according to its preferred embodiment, but it is to be understood that variations and/or modifications may be made by those skilled in the art without for this reason departing from the relative scope of protection, as defined by the appended claims.

The invention claimed is:

1. A method for modifying one or more video frames of a digital video stream to be displayed on a display area (A), wherein:

a right eye reference system is associated with a right eye, said right eye reference system being a three-dimensional Cartesian reference system, integral with an eyeball of said right eye, and has an origin ($O_1$) in the center a cornea of said right eye and comprises a first axis ($x_1$), a second axis ($y_1$) and a third axis ($z_1$), wherein said second axis ($y_1$) is orthogonal to an interpupillary axis (B), wherein said interpupillary axis (B) is a straight line passing through the center of the right eye cornea and to the center of a left eye cornea, and said third axis ($z_1$) coincides with a first visual axis (V1), wherein said first visual axis (V1) is a straight line passing through the center of the right eye cornea and an eye fixation point (P), wherein said eye fixation point (P) is a point of said display area (A) observed by a person, said display area (A) being part of a stereoscopic or autostereoscopic video system, a left eye reference system is associated with a left eye, said left eye reference system being a three-dimensional Cartesian reference system, integral with an eyeball of said left eye, having an origin ($O_2$) in the center of said left eye cornea and comprising a first axis ($x_2$), a second axis ($y_2$) and a third axis ($z_2$), wherein said second axis ($y_2$) is orthogonal to said interpupillary axis (B) and said third axis ($z_2$) coincides with a second visual axis (V2), where said second visual axis (V2) is a straight line passing through the center of said left eye cornea and said eye fixation point (P), a display reference system is associated with said display area (A), said display reference system being a three-dimensional Cartesian reference system having an origin (O) in the center of said display area (A) and comprising a first axis (x), a second axis (y), and a third axis (z), wherein said first axis (x) is horizontal and said third axis (z) is perpendicular to a display plane, wherein said visualization plane is a plane passing through said display area and arranged in such a way that said display area (A) belongs to said display plane, said method comprising:

acquiring a first digital video stream (FD1), wherein said first digital video stream comprises a succession of first video frames ($FD1_1$, $FD1_2$ ... $FD1_N$);

identifying with respect to said first digital video stream (FD1)

for the right eye the shape, size and position of at least one first portion of video frame of at least one first video frame ($FD1_1$, $FD1_2$ ... $FD1_N$) in correspondence of which at least one first visual defect is perceived by said person, wherein shape, size and position of said at least one first portion of video frame are determined when said right eye reference system has the origin ($O_1$) in a predetermined first position and a predetermined first orientation such that the following predetermined first conditions are met:

said eye fixation point (P) coincides with the center of said display area (A), said right eye is at a predetermined first distance (D1) from said display area (A), and said first axis ($x_1$) and said second axis ($y_1$) of said right eye reference system are parallel respectively to said first axis (x) and said second axis (y) of said display reference system;

and/or for the left eye the shape, size and position of at least one second portion of video frame of at least one first video frame ($FD1_1$, $FD1_2$ . . . $FD1_N$) in correspondence of which at least one second visual defect is perceived by said person, where shape, size and position of said at least one second portion of video frame are determined when said left eye reference system has the origin ($O_2$) in a predetermined second position and a predetermined second orientation such that the following predetermined second conditions are met:

said eye fixation point (P) coincides with the center of said display area (A), said left eye is at a predetermined second distance (D2) from said display area (A), and said first axis ($x_2$) and said second axis ($y_2$) of said left eye reference system are parallel respectively to said first axis (x) and said second axis (y) of said display reference system;

determining for said at least one first portion of video frame of said at least one first video frame ($FD1_1$, $FD1_2$ . . . $FD1_N$), one or more first digital filters configured to change the value of one or more pixels of said at least one first portion of video frame, each of which is associated with a respective predetermined first portion of video frame, and/or for said at least one second portion of video frame of said at least one first video frame ($FD1_1$, $FD1_2$ . . . $FD1_N$), one or more second digital filters configured to change the value of one or more pixels of said at least one second portion of video frame, each of which is associated with a respective predetermined second portion of video frame;

configuring for the right eye, a right correction scheme ($SC_{DX}$) comprising said one or more first digital filters, wherein said right correction scheme ($SC_{DX}$) is a first data structure configured to modify said at least one first portion of video frame, wherein said first data structure comprises information relating to said one or more first digital filters, the information relating to said shape, size and position of each of said first portions of video frame and information relating to the associations of said first portions of video frame with each of said first digital filters; said right correction scheme ($SC_{DX}$) having a graphic format so as to be displayed with a predetermined first image, wherein one or more portions of said predetermined first image are associated with a respective first digital filter and each first digital filter is associated with a respective predetermined first portion of video frame, and/or for the left eye, a left correction scheme ($SC_{SX}$) comprising said one or more second digital filters, wherein said left correction scheme ($SC_{SX}$) is a second data structure configured to modify said at least one second portion of video frame, wherein said second data structure comprises information relating to said one or more second digital filters, the information relating to said shape, size and position of each of said second portions of video frame and information relating to associations of said second portions of video frame with each of said second digital filters; said left correction scheme ($SC_{SX}$) having a graphic format so as to be displayed with a predetermined second image, wherein one or more portions of said predetermined second image are associated with a respective second digital filter and each second digital filter is associated with a respective predetermined second portion of video frame;

acquiring a second digital video stream (FD2), wherein said second digital video stream (FD2) comprises a succession of second video frames ($FD2_1$, $FD2_2$ . . . $FD2_N$), said second video frames ($FD2_1$, $FD2_2$ . . . $FD2_N$) of said second digital stream (FD2) being video frames referring to a visual content displayable on said display area (A);

calculating for the right eye, a first position of the origin ($O_1$) and a first orientation of said right eye reference system with respect to said display reference system, and/or for the left eye, a second position of the origin ($O_2$) and a second orientation of said left eye reference system with respect to said display reference system;

comparing with reference to said right eye, the first position of the origin ($O_1$) of said right eye reference system with said predetermined first position of the origin ($O_1$) in the predetermined first conditions to verify whether said first position of the origin ($O_1$) is different from said predetermined first position, and/or the first orientation of said right eye reference system with said predetermined first orientation in the predetermined first conditions to verify whether said first orientation is different from said predetermined first orientation, and/or with reference to said left eye, the second position of the origin ($O_2$) of said left eye reference system with the predetermined second position of the origin ($O_2$) in the predetermined second conditions to verify if said second position of the origin ($O_2$) is different from said predetermined second position, and/or the second orientation of said left eye reference system with said predetermined second orientation in the predetermined second conditions to verify if said second orientation is different from said predetermined second orientation;

in response to determining that said first position of the origin ($O_1$) of said right eye reference system is different from said predetermined first position of the origin ($O_1$) and/or said first orientation of said right eye reference system is different from said predetermined first orientation, reconfiguring said right correction scheme ($SC_{DX}$) on the basis of said first position of the origin ($O_1$) and/or said first orientation, so that said one or more first digital filters are applied to respective first portions of video frame, different from said predetermined first portions of video frame, and/or in response to determining that said second position of the origin ($O_2$) of said left eye reference system is different from said predetermined second position of the origin ($O_2$) and/or said second orientation is different from said predetermined second orientation, reconfiguring said left correction scheme ($SC_{SX}$) based on said second position of the origin ($O_2$) and/or said second orientation, so that said one or more second digital filters are applied to one or more respective second portions of video frame, different from said predetermined second portions of video frame;

applying said right correction scheme ($SC_{DX}$) to at least one second video frame ($FD2_1$, $FD2_2$ ... $FD2_N$) of said second digital video stream (FD2) in such a way that one or more first digital filters are applied to at least one first portion of video frame, so as to obtain a right digital stream ($FD2_{DX}$) for the right eye, different from said second digital video stream (FD2), wherein said right digital stream ($FD2_{DX}$) comprises at least one second modified video frame ($FD2_1'$, $FD2_2'$ ... $FD2_N'$), and/or said left correction scheme ($SC_{SX}$) to at least one second video frame ($FD2_1$, $FD2_2$ ... $FD2_N$) of said second digital video stream (FD2) in such a way that said one or more second digital filters are applied to at least one second portion of video frame, so as to obtain a left digital stream ($FD2_{SX}$) for the left eye, different from said second digital video stream (FD2), wherein said left digital stream ($FD2_{SX}$) comprises at least one further second modified video frame ($FD2_1''$, $FD2_2''$ ... $FD2_N''$);

generating a multiview digital video stream (MV) comprising a first sequence of video frames associated with said second digital video stream (FD2) or said right digital video stream ($FD2_{DX}$), and a second sequence of video frames associated with said second digital video stream (FD2) or said left digital video stream ($FD2_{SX}$); and displaying said multiview digital video stream (MV) by said stereoscopic or autostereoscopic video system in such a way that said first sequence of video frames of said multiview digital video stream (MV) be seen by said right eye and said second sequence of video frames of said multiview video digital stream (MV) be seen by said left eye (2).

2. The method according to claim 1, wherein in response to said right eye and/or said left eye moving and/or a head of said person moving, said method further comprises:

calculating for said right eye, a further first position of the origin ($O_1$) and a further first orientation of said right eye reference system with respect to said display reference system, and/or for said left eye, a further second position of the origin ($O_2$) and a further second orientation of said left eye reference system with respect to said display reference system;

comparing said further first position of the origin ($O_1$) of said right eye reference system with said predetermined first position of the origin ($O_1$) in the predetermined first conditions to verify if said further first position of the origin ($O_1$) of said right eye reference system is different from said predetermined first position and/or said further first orientation of said right eye reference system with said predetermined first orientation in the predetermined first conditions in order to verify if said further first orientation is different from said predetermined first orientation, and/or said further second position of the origin ($O_2$) of said left eye reference system with said predetermined second position of the origin ($O_2$) in the predetermined second conditions to verify if said further second position of the origin ($O_2$) is different from said predetermined second position, and/or said further second orientation of said left eye reference system with said predetermined second orientation in the predetermined second conditions in order to verify if said further second orientation is different from said predetermined second orientation;

for said right eye, comparing said further first position of the origin ($O_1$) of said right eye reference system with said first position to verify if said further first position of the origin ($O_1$) is different from said first position of the origin ($O_1$), when said further first position of the origin ($O_1$) of said right eye reference system is different from said predetermined first position of the origin ($O_1$) in the predetermined first conditions, and/or said further first orientation of said right eye reference system with said first orientation to verify if said further first orientation is different from said first orientation, when said further first orientation of said right eye reference system is different from said predetermined first orientation in the predetermined first conditions, and/or for said left eye, comparing said further second position of the origin ($O_2$) of said left eye reference system with said second position of the origin ($O_2$) to determine whether said further second position of the origin ($O_2$) is different from said second position of the origin ($O_2$), when said further second position of the origin ($O_2$) of said left eye reference system is different from said predetermined second position of the origin ($O_2$) in the predetermined second conditions, and/or said further second orientation of said eye left reference system with said second orientation to verify if said further second orientation is different from said second orientation when said further second orientation of said left eye reference system is different from said predetermined second orientation in the predetermined second conditions;

reconfiguring said right correction scheme ($SC_{DX}$) based on said further first position of the origin ($O_1$) as calculated, when said further first position of the origin ($O_1$) of said right eye reference system is different from said first position of the origin ($O_1$), and/or on the basis of said further first orientation as calculated, when said further first orientation is different from said first orientation, and/or reconfiguring said left correction scheme ($SC_{SX}$) based on said further second position of the origin ($O_2$) as calculated, when said further second position of the origin ($O_2$) of said left eye reference system is different from said second position of the origin ($O_2$), and/or on the basis of said further second orientation as calculated, when said further second orientation is different from said second orientation.

3. The method according to claim 1, wherein each of said first video frames is an Amsler grid.

4. The method according to claim 1, wherein each first digital filter is graphically represented in a respective portion of said predetermined first image of said right correction scheme ($SC_{DX}$) and each second digital filter is represented graphically in a respective further portion of said predetermined second image of said left correction scheme ($SC_{SX}$).

5. The method according to claim 1, wherein said visual content of said second digital video stream (FD2) is an image or a television broadcast or a live video or a recorded video or a video output of a computer.

6. A system for modifying one or more frames of a digital video stream displayable on a display area (A), said system comprising:
   a first digital video source (SV1) configured to provide a first digital video stream (FD1), wherein said first digital video stream (FD1) comprises a succession of first video frames ($FD1_1$, $FD1_2$ ... $FD1_N$); said one or more first digital filters and/or said one or more second digital filters being determined with respect to said first digital video stream (FD1),
   a second digital video source (SV2) configured to provide a second digital video stream (FD2), wherein said second digital video stream (FD2) comprises a succession of second video frames ($FD2_1$, $FD2_2$ ... $FD2_N$); said second video frames ($FD2_1$, $FD2_2$ ... $FD2_N$) of said second digital stream (FD2) being related to a visual content displayable on said display area (A);
   a tracking system configured to track an eye fixation point (P) in said display area (A), the tracking system further configured to calculate:
      for the right eye, a first position of the origin ($O_1$) and a first orientation of a right eye reference system with respect to a display reference system, said right eye reference system being a three-dimensional Cartesian reference system, integral with an eyeball of said right eye, having an origin ($O_1$) in a center of a cornea of said right eye and comprising a first axis ($x_1$), a second axis ($y_1$) and a third axis ($z_1$), wherein said second axis ($y_1$) is orthogonal to an interpupillary axis (B), wherein said interpupillary axis (B) is a straight line passing through the center of the cornea of the right eye and the center of the left eye cornea, and said third axis ($z_1$) coincides with a first visual axis (V1), wherein said first visual axis (V1) is a straight line passing through the center of the cornea of the right eye and said eye fixation point (P), a display reference system is associated with said display area (A), said display reference system being a three-dimensional Cartesian reference system having an origin (O) in the center of said display area (A) and comprising a first axis (x), a second axis (y), and a third axis (z), wherein said first axis (x) is horizontal and said third axis (z) is perpendicular to a display plane, wherein said display plane is a plane passing through said display area (A) arranged in such a way that said display area (A) belongs to said display plane,
   and/or
      for the left eye, a second position of the origin ($O_2$) and a second orientation of said left eye reference system with respect to said display reference system, said left eye reference system being a three-dimensional Cartesian reference system, integral with the eyeball of said left eye (2), having an origin ($O_2$) in the center of said left eye cornea and comprising a first axis ($x_2$), a second axis ($y_2$) and a third axis ($z_2$), wherein said second axis ($y_2$) is orthogonal to said interpupillary axis (B) and said third axis ($z_2$) coincides with a second visual axis (V2), wherein said second visual axis (V2) is a straight line passing through the center of said left eye cornea (2) and said eye fixation point (P);
   a correction device adapted to modify the video frames of a digital video stream on the basis of visual defects perceived due to a degenerative disease of the retina, in which are stored a right correction scheme ($SC_{DX}$) comprising one or more first digital filters configured to change the value of one or more pixels of at least one first portion of video frame, wherein each first digital filter is associated with at least one predetermined first portion of video frame, and/or a left correction scheme ($SC_{SX}$) comprising one or more second digital filters configured to change the value of one or more pixels of at least one second portion of video frame, wherein each second digital filter is associated with at least one predetermined second portion of video frame, said right correction scheme ($SC_{DX}$) being a first data structure comprising information relating to said one or more first digital filters, the information related to shape, size and position of at least one first portion of video frame at which at least one first visual defect is perceived by a person, and information on associations related to said first portions of video frame with each of said first digital filter; said right correction scheme ($SC_{DX}$) having a graphic format so as to be displayed with a predetermined first image, wherein one or more portions of said predetermined first image are associated with a respective first digital filter and each first digital filter is associated with a respective predetermined first portion of video frame, said left correction scheme ($SC_{SX}$) being a second data structure comprising information relating to said one or more second digital filters, the information related to shape, size and position of at least one second portion of video frame at which at least one second visual defect is perceived by a person, and information relating to the associations of said second portions of video frame with each of said second digital filters; said left correction scheme ($SC_{SX}$) having a graphic format so as to be displayed with a predetermined second image, wherein one or more portions of said predetermined second image are associated with a respective second digital filter and each second digital filter is associated with a respective predetermined second portion of video frame; and
   a stereoscopic or autostereoscopic video system, wherein said stereoscopic or autostereoscopic video system comprises a display device provided with said display area (A),
   wherein:
      said correction device is connected to said first digital video source (SV1) and said second digital video source (SV2), as well as to said tracking system and to said stereoscopic or autostereoscopic video system, and is configured to:
      acquire said second digital video stream (FD2), wherein said second digital video stream comprises a succession of second video frames ($FD2_1$, $FD2_2$ ... $FD2_N$);

receive from said tracking system
with reference to said right eye, said first position of the origin ($O_1$) and/or said first orientation of said right eye reference system, and/or
with reference to said left eye, said second position of the origin ($O_2$) and/or said second orientation of a left eye reference system;
compare
with reference to said right eye, said first position of the origin ($O_1$) of said right eye reference system with a predetermined first position of the origin ($O_1$) to determine whether said first position of the origin ($O_1$) is different from said predetermined first position, and/or said first orientation of said right eye reference system with a predetermined first orientation in order to verify if said first orientation is different from said predetermined first orientation, said predetermined first position of the origin ($O_1$) and said predetermined first orientation are such that the following predetermined first conditions are met:
said eye fixation point (P) coincides with the center of said display area (A),
said right eye is at a predetermined first distance (D1) from said display area (A), and
said first axis ($x_1$) and said second axis ($y_1$) of said right eye reference system are parallel respectively to said first axis (x) and said second axis (y) of said display reference system;
and/or
with reference to said left eye, said second position of the origin ($O_2$) of said eye left reference system with a predetermined second position of the origin ($O_2$) to determine whether said second position of the origin ($O_2$) is different from said predetermined second position, and/or said second orientation of said left eye reference system with a predetermined second orientation in order to verify if said second orientation is different from said predetermined second orientation, said predetermined second position of the origin ($O_2$) and said predetermined second orientation are such that the following predetermined second conditions are met:
said eye fixation point (P) coincides with the center of said display area (A),
said left eye is at a predetermined second distance (D2) from said display area (A), and
said first axis ($x_2$) and said second axis ($y_2$) of said left eye reference system are parallel respectively to said first axis (x) and said second axis (y) of said display reference system;
reconfigure said right correction scheme ($SC_{DX}$) on the basis of said first position of the origin ($O_1$) and/or said first orientation, so that said one or more first digital filters are applied to respective first portions of video frame, different from said predetermined first portions of video frame, when said first position of the origin ($O_1$) of said right eye reference system is different from said predetermined first position of the origin ($O_1$) and/or said first orientation of said right eye reference system is different from said predetermined first orientation, and/or reconfiguring said left correction scheme ($SC_{SX}$) based on said second position of the origin ($O_2$) and/or said second orientation, so that said one or more second digital filters are applied to one or more respective second portions of video frame, different from said predetermined second portions of video frame, when said second position of the origin ($O_2$) of said left eye reference system is different from said predetermined second position of the origin ($O_2$) and/or said second orientation is different from said predetermined second orientation;
applying
said right correction scheme ($SC_{DX}$) to at least one second video frame ($FD2_1$, $FD2_2$ ... $FD2_N$) of said second digital video stream (FD2) in such a way that said one or more first digital filters are applied to at least one first portion of video frame, so as to obtain a third digital video stream or right digital stream (FD2DX) for the right eye, different from said second digital video stream (FD2), wherein said right digital stream ($FD2_{DX}$) comprises at least one second modified video frame ($FD2_1'$, $FD2_2'$ ... $FD2_N'$), and/or
said left correction scheme ($SC_{SX}$) to at least one second video frame ($FD2_1$, $FD2_2$ ... $FD2_N$) of said second digital video stream (FD2) in such a way that said one or more second digital filters (12) are applied to at least one second portion of video frame, so as to obtain a left digital stream ($FD2_{SX}$) for the left eye, different from said second digital video stream (FD2), wherein said left digital stream ($FD2_{SX}$) comprises at least one further modified second video frame ($FD2_1''$, $FD2_2''$ ... $FD2_N''$);
generate a multiview digital video stream (MV) comprising a first sequence of video frames associated with said second digital video stream (FD2) or said right digital video stream ($FD2_{DX}$), and a second sequence of video frames associated with said second digital video stream (FD2) or said left digital video stream ($FD2_{SX}$); and
execute a video encoding compatible with said stereoscopic and autostereoscopic video system);
said stereoscopic or autostereoscopic video system is configured to:
receive as input said multiview digital video stream (MV), and
display said multiview digital video stream (MV) in such a way that said first sequence of video frames of said multiview digital video stream (MV) be seen by said right eye and said second succession of video frames of said multiview digital video stream (MV) be seen by said left eye.

7. The system according to claim 6, wherein said right correction scheme ($SC_{DX}$) comprises a plurality of said first digital filters, and said left correction scheme ($SC_{SX}$) comprises a plurality of said second digital filters.

8. The system according to claim 6, wherein each first digital filter is graphically represented in a respective portion of said predetermined first image of said right correction scheme ($SC_{DX}$) and each second digital filter is graphically represented in a respective further portion of said predetermined second image of said left correction scheme ($SC_{SX}$).

9. The system according to claim 6, wherein said second digital video source (SV2) is the same as said first digital video source (SV1).

10. The system according to claim 6, wherein said visual content is an image or a television broadcast or a live video or a recorded video or a video output of a computer.

* * * * *

UNITED STATES PATENT AND TRADEMARK OFFICE
CERTIFICATE OF CORRECTION

PATENT NO.        : 10,574,966 B2
APPLICATION NO.   : 16/096978
DATED             : February 25, 2020
INVENTOR(S)       : Carmelo Lodato Page 1 of 1

It is certified that error appears in the above-identified patent and that said Letters Patent is hereby corrected as shown below:

In the Claims

In Column 39, Line 16, Claim 6, after "more" insert --video--.

In Column 40, Line 9, Claim 6, after "cornea" delete "(2)".

In Column 42, Line 9, Claim 6, delete "applying" and insert --apply--.

In Column 42, Line 16, Claim 6, delete "(FD2DX)" and insert --(FD2$_{DX}$)--.

In Column 42, Line 49 (Approx.), Claim 6, after "eye" insert --(2)--.

Signed and Sealed this
Nineteenth Day of May, 2020

Andrei Iancu
*Director of the United States Patent and Trademark Office*